US007343016B2

(12) United States Patent
Kim

(10) Patent No.: US 7,343,016 B2
(45) Date of Patent: Mar. 11, 2008

(54) LINEAR INDEPENDENCE METHOD FOR NONINVASIVE ON-LINE SYSTEM IDENTIFICATION/SECONDARY PATH MODELING FOR FILTERED-X LMS-BASED ACTIVE NOISE CONTROL SYSTEMS

(75) Inventor: Benjamin Jung Kim, McClean, VA (US)

(73) Assignee: The Penn State Research Foundation, McClean, VA (US)

( * ) Notice: Subject to any disclaimer, the term of this patent is extended or adjusted under 35 U.S.C. 154(b) by 667 days.

(21) Appl. No.: 10/619,801

(22) Filed: Jul. 16, 2003

(65) Prior Publication Data

US 2004/0037430 A1 Feb. 26, 2004

Related U.S. Application Data

(60) Provisional application No. 60/397,526, filed on Jul. 19, 2002.

(51) Int. Cl.
*A61F 11/06* (2006.01)

(52) U.S. Cl. ................ 381/71.12; 381/71.1; 381/71.8; 381/71.11

(58) Field of Classification Search ............... 381/71.1, 381/71.11, 71.12, 71.8, 71.6
See application file for complete search history.

(56) References Cited

U.S. PATENT DOCUMENTS 4,677,676 A 6/1987 Eriksson ...................... 381/71
4,987,598 A * 1/1991 Eriksson .................. 381/71.11
5,940,519 A 8/1999 Kuo ........................ 381/71.11
6,418,227 B1 * 7/2002 Kuo ........................ 381/71.11
6,418,228 B1 7/2002 Terai et al. ................ 381/71.8
6,847,721 B2 * 1/2005 Zhang et al. ............ 381/71.11

OTHER PUBLICATIONS

L.J. Eriksson and M.C. Allie, "Use of Random Noise for On-Line Transducer Modeling in Adaptive Active Attenuation System," Journal of the Acoustical Society of America, vol. 88, 1989, pp. 797-802.

S.D. Sommerfeldt and J. Tichy, "Adaptive Control of a Two-Stage Vibration Isolation Mount," Journal of Acoustical Society of America, vol. 88, No. 2, 1990, pp. 938-944.

M.W.R.M. van Overbeek, "A Method To Identify The Secondary Path In Active Noise Control Systems," *Proc.Recent Advances in Active Control of Sound and Vibration*, 1991.

S.M. Kuo, M. Wang, and K. Chen. "Active Noise Control System with Parallel On-Line Error Path Modeling Algorithm," Noise Control Engineering Journal, vol. 39, No. 3, 1992, pp. 119-127.

(Continued)

*Primary Examiner*—Vivian Chin
*Assistant Examiner*—Devona E Faulk
(74) *Attorney, Agent, or Firm*—Ohlandt, Greeley, Ruggiero & Perle, L.L.P.

(57) ABSTRACT

A method for noninvasive on-line secondary path modeling for the filtered-X LMS algorithm actively controls periodic noise. The method, based in the frequency domain, uses the concept of linear independence of two equations/two unknowns to arrive at the secondary path estimate. Linear independence of the two equations is achieved by adjusting the control filter output via the filter coefficients prior to the acquisition of the second set of data corresponding to the second equation.

9 Claims, 24 Drawing Sheets

OTHER PUBLICATIONS

R.L. Clark, "A novel approach to feedforward higher-harmonic control," J. Accoust. Soc. Am. 96 (2), Pt. 1, Aug. 1994, pp. 926-936.

D.L. Kewley, R.L. Clark and S.C. Southward, "Feedforward Control Using the Higher-Harmonic, Time-Averaged Gradient Descent Algorithm," Journal of the Acoustical Society of America, vol. 97, 1995, pp. 2892-2905.

S. Kuo, K.M. Chung, "Secondary Path Delay Estimation Technique For Periodic Active Noise Control," *Proceedings of Active 95*, 1995.

N. Saito, T. Sone, T. Ise and M. Akiho, "Conditions For Optical On-Line Identification Of Secondary Path In Active Noise Control Systems," *Proceedings of Active 95*, 1995.

S. M. Kuo and X.H. Jiang, "Secondary Path Modeling Technique For Transformer Active Noise Control," *Proceedings of Inter-noise*, 1999.

W.C. Nowlin, "Noninvasive system identification for multichannel broadband active noise control," J. Acoust. Soc. Am. 107 (4), Apr. 2000, pp. 2049-2060.

S. Kim and Y. Park, "On-Line Fundamental Frequency Tracking Method for Harmonic Signal and Application to ANC," Journal of Sound and Vibration (2001), pp. 681-691.

X. Qiu and C.H. Hansen, "An Algorithm For Active Control of Transformer Noise with On-Line Cancellation Path Modelling Based on the Perturbation Method," Journal of Sound and Vibration, vol. 240, No. 4, 2001, pp. 647-665.

S.M. Lee, H.J. Lee, C.H. Yoo, D.H. Youn and I.W. Cha, "An Active Noise Control Algorithm for Controlling Multiple Sinusoids," Journal of the Acoustical Society of America, vol. 104, 1998, pp. 248-254.

M. Zhang, H. Lan and W. Ser, "A Modified Algorithm For ANC Secondary Path Modeling," *Proceedings of Internoise*, 1999.

Y. Maeda and T. Yoshida, "An Active Noise Control Without Estimation of Secondary Path—ANC Using Simultaneous Perturbation," *Proceedings of Active*, 1999, pp. 985-994.

* cited by examiner

LINEAR INDEPENDENCE METHOD FOR NONINVASIVE ON-LINE SYSTEM IDENTIFICATION/SECONDARY PATH MODELING FOR FILTERED-X LMS-BASED ACTIVE NOISE CONTROL SYSTEMS

CROSS-REFERENCE

The present application claims priority to Provisional Application Ser. No. 60/397,526, filed Jul. 19, 2002, entitled "Method for noninvasive on-line secondary path modeling for the filtered-X LMS algorithm for active control of periodic noise."

BACKGROUND OF THE INVENTION

1. Field of the Invention

The present invention generally relates to active control of periodic noise. In particular, it relates to noninvasive on-line secondary path modeling for the filtered-X LMS algorithm.

2. Description of the Related Art

In an effort to overcome problems unsolvable in the practical sense using passive techniques, typically the attenuation of undesired low frequency noise, active noise control has received considerable interest in recent decades. The physical principles involved in the control of sound by active techniques had long been established and understood. However, it was not until the 1980's that the advances in signal processing, actuator, and sensor technology allowed for extensive research and practical implementation of these techniques. The history of active noise and vibration control reveals that both interest and progress in this area have been closely associated with the development of relevant technology. This is attributed to the accurate amplitude and phase matching that is required of an active control system to produce high degrees of attenuation of the unwanted noise or vibration. Active noise control had become one of the most popular research topics in engineering with hundreds of journal papers covering dozens of associated topics reaching the academic press each year.

Despite the vast research effort, commercial success in applying active control technology, apart from active headsets and the occasional HVAC and aircraft implementations, has been extremely limited. This failure to "take off" has caused interest in active noise control to wane in recent years. The inability of controllers to guarantee performance and stability in all operating conditions renders the current active noise and vibration control technology essentially stillborn, preventing the technology from achieving broad applicability. Part of the difficulty has been in developing algorithms that perform robustly in applications where signals and environments are continuously changing. The ideal noise control system can track and cancel non-stationary signals and account for environmental changes simultaneously, all of this without the injection of any foreign noise into the system for the purpose of secondary path modeling, also known generally as system identification. However, the issue of stability and real-time adaptation has proven most arduous in achieving the goal of noise attenuation via a secondary source.

The filtered-X LMS algorithm is a modified form of the LMS algorithm for use when there is a non-unity transfer function in the secondary path following the adaptive filter which is the case for most practical ANC applications. In this formulation the reference signal is filtered by the secondary path estimate. Burgess coined the term "filtered-X" for the adaptive algorithm since the reference signal was often labeled x(t).

The filtered-X LMS algorithm requires an estimate of the secondary, or cancellation, path in order to compensate for any signal delays and gains associated with the path. This is done in essence to align the primary disturbance and the secondary disturbance at the error sensor in the eyes of the LMS algorithm. A sufficiently accurate model of this path is crucial to the success of the algorithm.

There are two basic approaches to this problem. One approach is the off-line approach where the path is modeled prior to active control system startup. The drawback to this approach is that the secondary path model can not evolve as the secondary path evolves due to such changes as temperature, humidity, air velocity (in a duct), all of which affects the sound speed and hence the delay in the path; the frequency response of system components tend to change due to temperature also, as well as age and operating conditions. If the plant can not track the changes in the system the performance of the algorithm suffers.

The other approach is to model the path on-line as the system is running. This would allow the secondary path model to track the secondary path as it evolves during system operation. This of course is favorable and necessary for the filtered-X LMS algorithm to work properly. There are basically two approaches for on-line secondary path modeling: invasive and noninvasive. The former involves the addition of what is often referred to as an interrogation signal; random noise or chirps of sufficient bandwidth are added to the system through the control source to determine directly the frequency response of this path. Besides the counterproductive appearance of injecting auxiliary noise for the purposes of noise control, this approach has been shown to suffer from misalignment in the secondary path estimates and long convergence times. Therefore the preferred approach is non-invasive wherein the control signals are utilized to perform system identification. However, this has proven to be non-trivial as this is still a topic of numerous papers published in active noise control.

No existing algorithm has been proven to provide consistently accurate secondary path models in a noninvasive fashion. Inaccurate estimates are the cause of instability in the application of the filtered-X LMS algorithm. The present invention addresses the challenge of highly accurate but still noninvasive on-line secondary path modeling.

Previous noninvasive algorithms have utilized iterative search methods that have proven unsuccessful in delivering sufficiently accurate secondary path models for use by the filtered-X LMS-based control system, especially in time-varying systems, resulting in poor performance and instability.

SUMMARY OF THE INVENTION

An active noise and vibration control system for generating an antinoise signal to attenuate a narrowband noise signal propagating through a medium, the active noise and vibration control system performing on-line noninvasive secondary path modeling, the system, comprises a reference sensor, a secondary source, an error sensor and a controller. The reference sensor operates to receive a reference signal related to a primary noise and to generate a primary signal in response. The secondary source operates to generate an antinoise corresponding to a secondary signal that attenuates the primary noise. The error sensor operable to receive a residual signal that is the superposition of the primary noise and a secondary noise at the location of the error sensor, and to generate an error signal in response thereto. The controller operates to receive the primary signal and the error signal and to generate the secondary signal while performing on-line noninvasive secondary path modeling. The controller comprises an on-line noninvasive secondary path modeler operable to receive the primary signal, the secondary signal, and the error signal for the purpose of calculating the secondary path model.

The system further comprises an online noninvasive secondary path modeler. The modeler captures two data sets comprising a reference signal, an error signal and generated secondary signal, to calculate a transfer function of the secondary path, and to alter an output of a secondary source by adjusting output filter coefficients in amplitude, in phase, or in both amplitude and phase between acquisition of the data sets, thereby imposing linear independence on the data sets. The secondary path modeler uses the data sets to calculate a secondary path model algebraically in a system of two equations-two unknowns. An equation derived from the algebraic calculation is modified to account for spectral leakage and narrowband effects. The derived equation is modified to account for multiple frequency signals, and frequency spectrum is divided into subbands to scale each frequency component separately.

A feedforward active noise and vibration control system comprises a controller. The controller receives a primary signal and an error signal and generating a secondary signal in response thereto. The controller comprises an on-line noninvasive secondary path modeler and an adaptive filter utilizing block time domain or equivalent frequency domain processing. The system further comprises an online noninvasive secondary path modeler. The modeler captures two data sets comprising a reference signal, an error signal and generated secondary signal, to calculate a transfer function of the secondary path, and to alter an output of a secondary source by adjusting output filter coefficients in amplitude, in phase, or in both amplitude and phase between acquisition of the data sets, thereby imposing linear independence on the data sets. The secondary path modeler uses the data sets to calculate a secondary path model algebraically in a system of two equations-two unknowns. An equation derived from the algebraic calculation is modified to account for spectral leakage and narrowband effects.

There is a method for calculating an accurate secondary path model. A secondary path modeler is employed to capture two data sets comprising a reference signal, an error signal and generated secondary signal. The secondary path modeler is used to calculate the transfer function of a secondary path. The secondary path modeler is used to alter an output of a secondary source by adjusting output filter coefficients in amplitude, in phase, or in both amplitude and phase between acquisition of the data sets, thereby imposing linear independence on the data sets. The secondary path modeler is noninvasive. The secondary path modeler uses the data sets to calculate the secondary path model algebraically in a system of two equations-two unknowns. An equation derived from the algebraic calculation is modified to account for spectral leakage and narrowband effects. The derived equation is modified to account for multiple frequency signals, and frequency spectrum is divided into subbands to scale each frequency component separately.

There is a method for noninvasive on-line secondary path modeling for a filtered-X LMS algorithm for the active control of periodic noise. Linear independence of two equations and two unknowns is used to arrive at a secondary path estimate in a secondary path model. Linear independence is achieved by adjusting an output of a control filter via filter coefficients prior to acquisition of a second set of data corresponding to a second of the two equations. Operation of the control filter is stable so that reliable noise cancellation performance is achieved. The secondary path model is based in a frequency domain. Testing is performed on a transducer-less electrical system for validation of active noise control algorithms. The transducer-less electrical system comprises a summing junction circuit and a computer housing an adjustable filter and signal generators. Validating is performed using sinusoidal and dual-frequency signals. System changes are tracked by conducting tests when frequencies are shifted and the secondary path is changing. Secondary path estimates are compared to estimates ascertained using an LMS-based adaptive filer. The summing junction simulates an interference between a primary and a secondary disturbance. The adjustable filter provides a time-varying secondary path. The signal generators provide a reference signal.

There is a method for on-line noninvasive secondary path modeling. A reference sensor receives a reference signal related to a primary noise. The reference sensor generates a primary signal in response to the reference signal. A secondary source generates an antinoise corresponding to a secondary signal that attenuates the primary noise. An error sensor receives a residual signal that is the superposition of the primary noise and a secondary noise at the location of the error sensor. An error signal is generated in response thereto. A controller receives the primary signal and the error signal. The controller generates the secondary signal while performing on-line noninvasive secondary path modeling. The controller comprises an on-line noninvasive secondary path modeler operable to receive the primary signal, the secondary signal, and the error signal for the purpose of calculating the secondary path model.

There is a method for feedforward active noise and vibration control. A controller receives a primary signal and an error signal and generates a secondary signal in response thereto. The controller comprises an on-line noninvasive secondary path modeler and an adaptive filter utilizing block time domain or equivalent frequency domain processing.

DETAILED DESCRIPTION OF THE INVENTION

Figure 1:
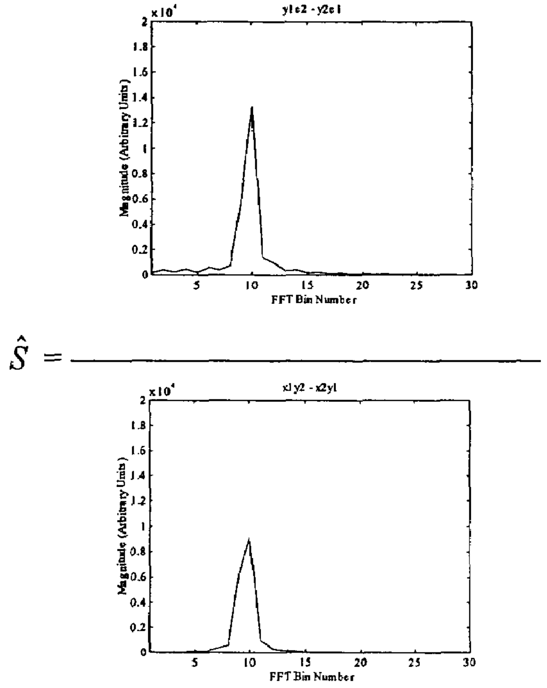
FIG. 1 is a visual representation of equation (13b) for a sinusoidal signal.

The present invention describes a robust on-line and noninvasive secondary path modeling algorithm for periodic signals to work in tandem with the established filtered-X LMS algorithm, which requires a model of the secondary path, for active noise control. The on-line secondary path modeling algorithms of the past have either mandated the injection of random noise (an "invasive" approach) which is generally not desired for active noise control or have been insufficient in providing an accurate enough secondary path model for stability in time-varying systems when utilizing a noninvasive scheme. In this invention, the most well-known noninvasive algorithm, referred to as the overall modeling algorithm, was shown to provide grossly inaccurate secondary path estimates and exhibit seemingly chaotic behavior due to its design, facts that account for its unstable and unpredictable nature experienced by users of this algorithm. The overall algorithm is such that there are an infinite number of solutions that satisfy its cost function, the mean square of the modeling error; this was demonstrated above.

A review of the base algorithm, the filtered-X LMS algorithm, was given above including its derivation in the time domain and the significance of the secondary path model, a requisite of the algorithm. The filtered-X LMS algorithm was then formulated for frequency domain implementation. The frequency domain implementation offers significant savings in computation costs, savings that increase as the filter lengths increase. This implementation is useful for the purposes of this invention since the formulation of the present method of secondary path modeling is done in the frequency domain.

Errors in the secondary path models, or plant estimation errors, and how they affect the performance of the filtered-X LMS algorithm are described below. Studies had been done that revealed a tolerance of ±90° in the phase of the plant model. Anything outside this bound would cause the filtered-X LMS algorithm to diverge. Smaller step sizes would be necessary as the phase error deviated from 0° within these bounds. The magnitude of the plant model was stated in literature to not be as vital as the phase. It is the inventor's opinion that the magnitude is equally as important since the correct magnitude is never known a priori to adjust the step size accordingly. The formulation of the present method of secondary path modeling exploits the forgiving nature of the filtered-X LMS, specifically in the magnitude of the estimate. Thus, this information present thereafter is vital in investigating the performance of the present method.

The present method of on-line noninvasive secondary path modeling was formulated by the present invention, the basis of which is an elementary set of two equations and two unknowns incorporating two sets of data. These two equations are made linearly independent by forcing a change in the control filter coefficients prior to the gathering of the second data set.

A somewhat unprecedented method of testing active control algorithms is presented below. A circuit incorporating a summing junction was designed and built to simulate the superposition of the primary and secondary disturbances, be it acoustic in nature, mechanical, etc. To test the robustness of the present secondary path modeler, a computer with DSP hardware was utilized to provide a time-varying secondary path with frequency dependent gain and phase.

The test results are presented later. The present method was shown to provide unprecedented accuracy in the secondary path models for use by the filtered-X LMS algorithm for single-frequency signals and dual-frequency signals. The dual-frequency signals tested the generalized formulation for multiple-frequency signals where the DFT spectrum has to be divided into subbands, each subband containing a separate sinusoid, to scale the individual sinusoids independently in the secondary path transfer function estimate. The accuracy in the secondary path models contributed to the stability of the filtered-X LMS algorithm even as the system underwent change, either in frequency content of the signal or in the secondary path.

It is apparent from the formulation that a peak recognition algorithm must be implemented in order to divide the spectrum into the appropriately sized subbands for multiple frequency signals. Spectral peak recognition is a thoroughly-studied procedure and has been used extensively for speech recognition, pattern recognition, etc. Naturally the question arises concerning resolution, i.e. what happens when the peaks cannot be resolved to separate the peaks into their respective subbands? The two parameters, filter length and sampling rate, can help resolve this issue. Usually, the sound or vibration that is to be controlled is composed of harmonics, the fundamental frequency and its integer multiples. For these cases, it is the user's responsibility to determine the optimal resolution and sampling rate.

It is conceivable to use the control filter's own adaptation of the filter coefficients to provide the necessary control output perturbation to obtain the linear independent data set. This can theoretically provide an estimate of the secondary path at every iteration of the control filter.

The filtered-X LMS algorithm is well established as a robust active noise control solution granted that the secondary path estimate is sufficiently accurate during system operation and, if the system were to undergo change, that the properties of the system change slowly with respect to the speed of the controller and maintain linearity. The secondary path modeler described herein helps to resolve the issue of system plant inaccuracy. However, the most common cause of ANC failure is the introduction of nonlinearity or harmonic distortion by the secondary source regardless of the quality of the secondary path modeler. This harmonic distortion entering and re-entering the ANC control system via the error signal leads to runaway distortion and hence instability. The idea of hierarchical control architecture was introduced to help guarantee stability of the control system. It monitors the linearity of the control actuator as well as monitors the input and output of the DSP hardware to prevent overload. It also slows the filtered-X control while emphasizing system identification during suboptimal control by utilizing simple spectral metrics such as coherence that can clearly identify ANC controller performance. These are important features that should be implemented as stability would help further the commercial and military viability of future ANC systems.

Formulation of the Linear Independence Method

In a working active noise control system, the primary noise signal and the canceling secondary signal are coherent, alike in frequency and amplitude and opposite in phase—they must be since the underlying principle of active noise control states that the two signals should interfere destructively at the error sensor. However, without knowledge of either the primary or secondary path transfer function, it is impossible to identify and separate the contributions of the primary and the secondary sources to the error signal with one "snapshot" of data, which is essentially what the overall modeling technique has attempted to do.

It is straightforward to demonstrate this. Consider two sinusoids of equal frequency each with some specified phase and amplitude. The result of the superposition of the two sinusoids is a third sinusoid of equal frequency but with a particular phase and amplitude that depends on the relative phases and amplitudes of the summed sinusoids. If, however, the objective was to find the first two sinusoids with knowledge of only the third, the problem becomes nontrivial. In fact it is easily deduced that an infinite number of sets of sinusoids exist that will yield the third sinusoid. A simpler way to demonstrate this is to consider a linear equation, say p+s=1. If the object was to determine what two numbers were added to make up that particular sum of 1, even the casual observer would recognize that there are an infinite number of sets of solutions: {½, ½}, {3/10, 7/10}, {1/10, 9/10}, {1/100, 99/100}, {−½, 3/2}, {−1, 2} and so forth.

In any single channel active noise control system, the equation relating the contributions of the primary noise source and the secondary noise source to the error signal is $$[x(n)\otimes p(n)]+[y(n)\otimes s(n)]=e(n), \qquad (1)$$

where ⊗ denotes convolution; x(n) and y(n) are the reference and filter output signals, respectively; p(n) and s(n) represent the primary and secondary path impulse responses, respectively; and e(n) is the error signal. The quantity [x(n)⊗p(n)] corresponds to the primary source contribution to the error signal e(n) (reference signal x(n) traverses primary path p(n)) while the quantity [y(n)⊗s(n)] corresponds to the secondary source contribution (control filter output y(n) traverses secondary path s(n)). The filter output is related to the reference signal by the equation $$y(n)=\sum_{l=0}^{L-1} w_n(l)\times(n-l). \qquad (2)$$

where $w_n$ (l) is the lth coefficient of the FIR filter. Applying the Fourier transform to Eq. (1) gives $$[X(k)P(k)]+[Y(k)S(k)]=E(k), \qquad (3)$$

where k indicates the kth frequency bin. The readily observable and obtainable quantities are X(k), Y(k), and E(k), the inverse transforms of x(n), y(n), and e(n), respectively; these can be observed in one snapshot of data. The unknowns are P(k) and S(k), the primary path transfer function and secondary path transfer function, respectively. For the purpose of comparison Eq. (3) can be more simply written as $$\{XP+YS=E\}_k. \qquad (4)$$

The similarity between the aforementioned p+s=1 example and Eq. (4) is now evident: for P and S there exists an infinite set of solutions.

The Formulation

It was made apparent above that one equation is insufficient in determining a unique set of estimates for $\hat{P}(k)$ and $\hat{S}(k)$. It seems feasible to locate the correct set within the infinite pool of estimates that satisfy Eq. (1) by extrapolating to a set of two equations and two unknowns. Taking another snapshot of data allows for a set of two equations, $$X_A(k)P(k)+Y_A(k)S(k)=E_A(k) \qquad (5a)$$

$$X_B(k)P(k)+Y_B(k)S(k)=E_B(k), \qquad (5b)$$

where $\{X_A(k), Y_A(k), E_A(k)\}$ corresponds to the first snapshot of data and $\{X_B(k), Y_B(k), E_B(k)\}$ corresponds to the second snapshot of data. This formulation, of course, assumes that the transfer functions P and S do not change in between snapshots. This can be more conveniently presented in matrix notation like so:

$$\begin{bmatrix} E_A \\ E_B \end{bmatrix}_k = \begin{bmatrix} X_A & Y_A \\ X_B & Y_B \end{bmatrix}_k \begin{bmatrix} P \\ S \end{bmatrix}_k. \qquad (6)$$

It should be made clear that in matrix form there are as many of these matrix equations as there are frequency bins in the DFT's of the data vectors where the values in each matrix equation correspond to a bin of the DFT. So, for example, if the DFT's are 10-point DFT's, there would be ten matrix equations with one matrix equation corresponding to each of the ten bins of the DFT.

Conveniently, the problem of secondary path modeling is now reduced to a system of two equations and two unknowns where P and S are the unknowns. The estimates $\hat{P}(k)$ and $\hat{S}(k)$ can be solved for in a straightforward manner using matrix algebra giving $$\begin{bmatrix} \hat{P} \\ \hat{S} \end{bmatrix}_k = \begin{bmatrix} X_A & Y_A \\ X_B & Y_B \end{bmatrix}_k^{-1} \begin{bmatrix} E_A \\ E_B \end{bmatrix}_k, \tag{7}$$

An inversion of the matrix results in the matrix equation $$\begin{bmatrix} \hat{P} \\ \hat{S} \end{bmatrix}_k = \left\{ \frac{1}{X_A Y_B - Y_A X_B} \begin{bmatrix} Y_B & -Y_A \\ -X_B & X_B \end{bmatrix} \right\}_k \begin{bmatrix} E_A \\ E_B \end{bmatrix}_k. \tag{8}$$

The simplistic appearance of the solution, however, is deceiving as there are three critical problems inherent in the inversion of the 2×2 matrix. The first deals with the singularity issues of the matrix or, equivalently, the linear dependence of Eqs. (5a) and (5b). The second has to do with the sparse nature of the matrix for periodic signals. When considering narrowband signals, those matrices associated with the non-excited frequency bins will contain zeros or numbers approaching zero, rendering them noninvertible. The third has to do with problems due to leakage, also known as smearing, in the FFT's when a frequency of a signal happens to not fall directly on an FFT bin.

Linear Independence

According to linear theory, in order for the matrix to be invertible, it must be nonsingular. In order to ensure that the 2×2 matrix in Eq. (7) is nonsingular, the data sets corresponding to Eqs. (5a) and (5b) must be made linearly independent.

A unique and vital feature of the proposed method for secondary modeling renders certain that the inverse of the 2×2 matrix exists. If the control system is in steady state, the two snapshots will give a linearly dependent set of equations. However if, in this steady state system, a change is imposed on either X or Y in one of the data sets and this change is reflected in the error E, the equations will be linearly independent. The question is which quantity, X or Y, can be altered to ensure linear independence of the two data sets. In an active control system X is the reference signal that is taken from the primary noise source while Y is the filter output. Thus Y is the only quantity that can be adjusted "manually" via the filter coefficients. The reference signal can not be controlled since it is an observed parameter rather than an imposed one as Y is via the filter coefficients; this is the practical reason. The mathematical, other than practical, reason for adjusting Y rather than X is that Y is linearly dependent on X according to the frequency domain filter output equation, $$Y(k)=W(k)X(k), \tag{9}$$

so that any change imposed on X would yield a linear change in Y, a change that would render the two data sets still linearly dependent.

The output Y can be changed, either in phase or amplitude or both, by simply adjusting the filter coefficients related to W. For the two observations or data sets, the filter outputs are related to the reference signals as defined by $$Y_A(k)=W_A(k)X_A(k) \tag{10a}$$

$$Y_B(k)=W_B(k)X_B(k) \tag{10b}$$

Here $W_1 \neq W_2$ must be true for the two equations to be linearly independent (assuming the reference signal is in steady state). While there are numerous ways to adjust the filter coefficients, the simplest way to change one with respect to the other is to adjust the amplitude of the impulse response of one with respect to the other like so:

$$W_B(k)=(1+\epsilon)W_A(k). \tag{11}$$

This yields the following set of equations:

$$Y_A(k)=W_A(k)X_A(k) \tag{12a}$$

$$Y_B(k)=(1+\epsilon)W_A(k)X_B(k). \tag{12b}$$

While $\epsilon$ can be any real value, large or small (except zero of course), for the equations to be linearly independent, for active control systems only the minimum would be deemed necessary since adding a large $\epsilon$ to unity could yield a large secondary source output, contributing to the noise momentarily. The matrix equation of Eq. (8) can be rewritten as $$\hat{P}(k) = \frac{E_A(k)Y_B(k) - Y_A(k)E_B(k)}{X_A(k)Y_B(k) - Y_A(k)X_B(k)} \tag{13a}$$

$$\hat{S}(k) = \frac{X_A(k)E_B(k) - E_A(k)X_B(k)}{X_A(k)Y_B(k) - Y_A(k)X_B(k)}. \tag{13b}$$

where $Y_1=W_1X_1$ and $Y_2=(1+\epsilon)W_1X_2$. At first glance the two data sets, one of which reflects the change imposed on the system, will provide an exact estimate for both $\hat{P}$ and $\hat{S}$. However, subsequent glances will likely reveal how zero matrices resulting from narrowband signals can cause problems for those equations associated with the non-excited FFT bins. Any zeros in the FFT spectrum that result from the subtraction in the denominators will give a null set of solutions for those bins associated with those zeros. Bins that contain near-zeros will blow up. The third problem of leakage effects is less obvious.

The Zero Matrix Dilemma and Leakage Effects

As stated previously, FFT's of narrowband signals will result in a non-invertible 2×2 matrix found in Eq. (7) for those particular FFT bins containing zeros. Any zeros in the FFT spectrum that result from the subtraction in the denominator of Eqs. (13a) and (13b) will give a null set of solutions for those bins associated with those zeros upon inversion of the matrix.

The other problem deals with smearing or leakage due to the discrete nature of the digital implementation. If a snapshot of data, taken digitally, happens to contain a periodic signal, the likelihood of the snapshot window enclosing an exact integral multiple of wavelengths is slim to none. An exact integral multiple of wavelengths indicates a frequency that is exactly on an FFT frequency bin when an FFT of that snapshot is performed. In practice this almost never occurs. Frequencies are usually "off-bin", or lie somewhere in between FFT bins. When a non-integral multiple of wavelengths are contained in the snapshot window and an FFT is performed on the snapshot, the signal energy leaks into bins adjacent to frequency of the signal.

FIG. 1 graphically depicts Eq. (13b) and illustrates succinctly the difficulties at hand. Only the estimate Ŝ is considered for the sake of example. The plots were taken from a MATLAB simulation in which a sinusoid of 201 Hz with arbitrary phase was synthesized to act as the reference signal x(n). This signal was set equal to the desired signal d(n) (primary path is unity). The secondary path was given a 10 sample delay with a gain of unity. The signals were sampled at a rate of 24 kHz. The set of data consisted of a desired signal (or reference signal) and y'(n) each with an amplitude of one. The error signal reflects the superposition of these signals. The second set of data consisted of the same desired signal but a y'(n) with an amplitude that is 10% greater than in the previous data set. The error signal reflects the superposition of these signals.

Figure 2:
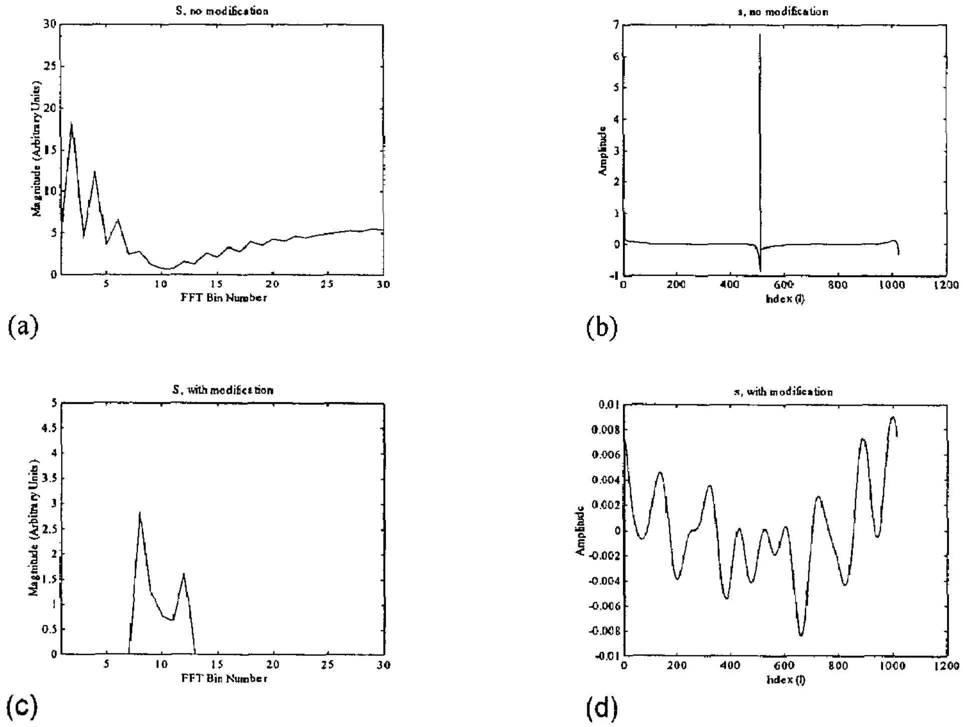
FIG. 2 is results for two methods of evaluating Eq. (13b), or the 'fraction' pictured in FIG. 21.

FIG. 1 is a visual representation of Eq. (13b) for sinusoidal signal. As pictured in FIG. 1, for a sinusoidal signal the numerator and denominator will each be a spectrum with energy across one localized set of frequency bins associated with frequency in the system. Bins 8 through 12 hold most of the 201 Hz signal energy. Zeros or near-zeros permeate the spectra of the denominator producing a null set of solutions for those frequency bins associated with the zeros when the division is performed for each bin. FIG. 2 shows results for two methods of evaluating Eq. (13b), or 'fraction' pictured in FIG. 1. A straight division of the spectra results in a spectrum shown in subfigure (a) of FIG. 2; its corresponding impulse response is given in subfigure (b) of FIG. 2, the inverse FFT (IFFT) of the spectrum. This does not yield the correct solution for Ŝ. This could be remedied by simply zeroing the bins that have "blown up" or have the potential to "blow up" or have a 0/0 in the solution for Ŝ. However, this is not without its own problems, problems that raise questions as to what amount of energy is insufficient or sufficient enough to warrant a zero in a bin. Subfigure (c) of FIG. 2 depicts the solution to Ŝ after having zeroed all the bins except for bins 8 through 12 (same was done to its negative frequency counterparts). Seen also in FIG. 2 is the problem posed by the leakage. The division for those bins with "sufficient" energy could also very well blow up if the magnitude of the bin in the denominator is smaller than the corresponding bin in the numerator. In this particular case, the magnitude does not blow up severely but the proportions of the adjacent bins relative to the major bin corresponding to 201 Hz do not reflect a 201 Hz in the IFFT, or impulse response, given in subfigure (d) of FIG. 2 (here only the magnitude is shown but the relative phases of the sinusoids associated with these adjacent bins affect the solution as well).

The inventor has determined that accurate phase was crucial to the success of the filtered-X LMS algorithm. While the magnitude of the plant estimate did not have to be exact, it was deemed that the magnitude be consistent in its inaccuracy, e.g. consistently 4 orders of magnitude greater, consistently 10 orders of magnitude lesser, consistently 10% to 50% of the correct magnitude of the estimate, etc. A consistent incorrectness in magnitude could always be compensated by an appropriately adjusted step size.

The present invention provides a secondary path model that is exact in phase but consistently less in magnitude. This promises a sufficient enough plant estimate for utilization by the filtered-X LMS algorithm.

Since the filtered-X LMS algorithm requires only the secondary path estimate Ŝ, only Eq. (13b) need be considered from this point forward. Eq. (13b) is restated as $$\hat{S}(k) = \frac{X_A(k)E_B(k) - E_A(k)X_B(k)}{X_A(k)Y_B(k) - Y_A(k)X_B(k)}. \tag{14}$$

to eliminate the minus sign. Noting that the FFT's are complex numbers, a routine complex conjugate multiply done on this expression will yield $$\hat{S}(k) = \frac{[X_A(k)E_B(k) - E_A(k)X_B(k)][X_A(k)Y_B(k) - Y_A(k)X_B(k)]^*}{[X_A(k)Y_B(k)]^2 + [Y_A(k)X_B(k)]^2}. \tag{15}$$

The denominator is now a vector of scalars, most of which are zeros or near-zeros for narrowband signals. Straight evaluation of this expression will yield the same result found in subfigure (a) of FIG. 2. The numerator happens to be a spectrum that represents the impulse response of the secondary path that is correct in phase. For sinusoidal signals (single frequency) its magnitude need only be scaled by a scalar value to yield the correct plant estimate. However, since this unique scalar value is largely unknown and dependent on leakage (which happens to be frequency and phase dependent), an approximation must be made that can scale the magnitude down to somewhere within the vicinity of the correct magnitude. The following expression results for the secondary path estimate:

$$\hat{S}(k) = \frac{[X_A(k)E_B(k) - E_A(k)X_B(k)][X_A(k)Y_B(k) - Y_A(k)X_B(k)]^*}{\{[X_A(k)Y_B(k)]^2 + [Y_A(k)X_B(k)]^2\}_{max}}. \tag{16}$$

Figure 3:
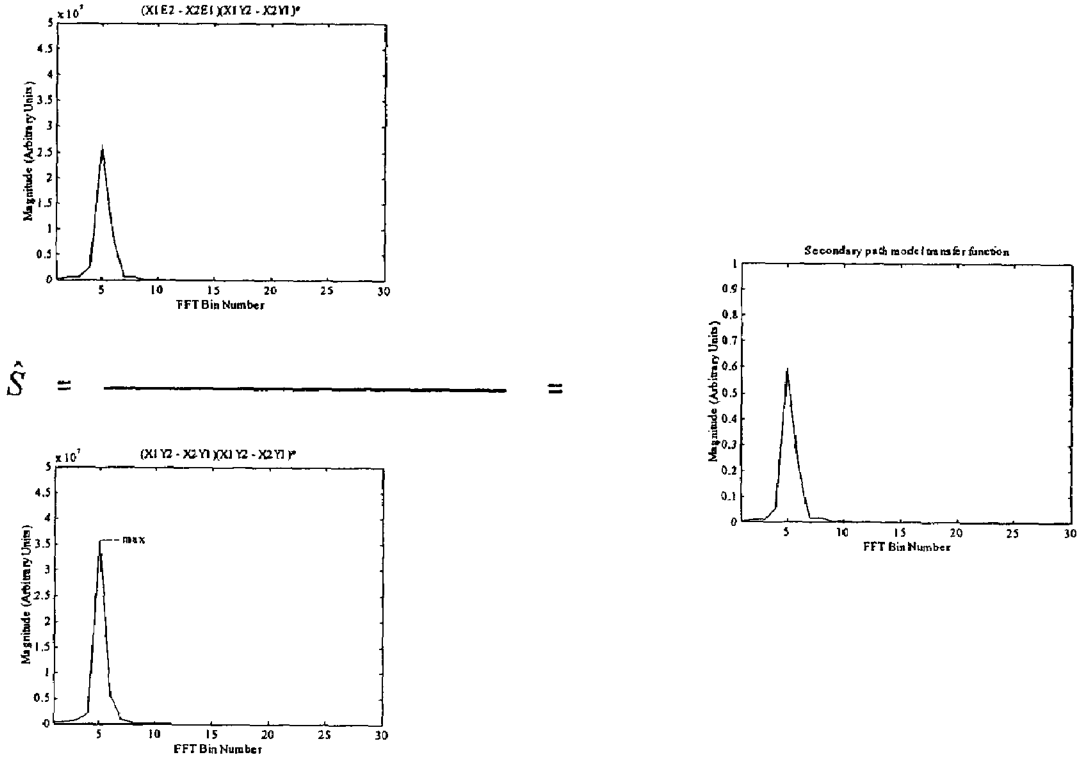
FIG. 3 is a visual representation of Eq. (16) for a simulation.
Figure 4:
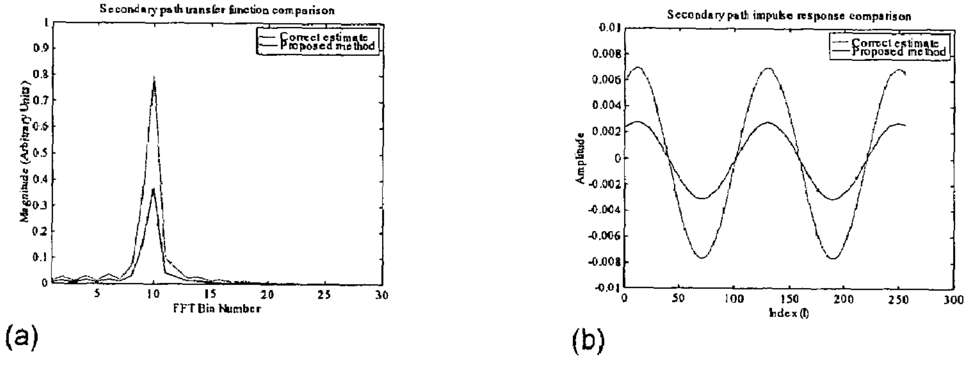
FIG. 4 is a comparison of correct estimate and calculated estimate using a method of the present invention.

For sinusoidal signals the magnitude of the numerator is scaled by the maximum scalar value represented in the vector in the denominator. As it turns out, according to the algorithm outlined above, this provides a magnitude in the estimate that is consistently less (within an order of magnitude) than the correct estimate. These comparisons are made extensively below. A visual representation of Eq. (16) for the simulation described above is given in FIG. 3. The maximum scalar value of the denominator indicated by "max" found in bin 5 is used to scale all the FFT bins in the numerator. The resulting secondary path transfer function model is given as well. A comparison of the transfer functions and corresponding impulse responses of the correct estimate and the estimate found using the proposed method is done in FIG. 4. It is apparent that the phase is exact. In this particular case, the magnitude is approximately ⅖th the magnitude of the correct estimate.

A simple extrapolation of the present invention will yield the general solution for multiple frequency signals. The sinusoidal case is a subset of this general solution. For multiple frequency signals, the spectrum must be divided into frequency bands, each band spanning bins associated with each sinusoid. Each band is then scaled by the maximum scalar value represented in the vector within that band in the denominator. So Eq. (15) can be generalized to accommodate multiple frequency signals like so:

$$\hat{S}_{B1}(k) = \frac{\{[X_A(k)E_B(k) - E_A(k)X_B(k)][X_A(k)Y_B(k) - Y_A(k)X_B(k)]^*\}_{B1}}{\{[X_A(k)Y_B(k)]^2 + [Y_A(k)X_B(k)]^2\}_{\max,B1}} \quad (17a)$$

$$\hat{S}_{B2}(k) = \frac{\{[X_A(k)E_B(k) - E_A(k)X_B(k)][X_A(k)Y_B(k) - Y_A(k)X_B(k)]^*\}_{B2}}{\{[X_A(k)Y_B(k)]^2 + [Y_A(k)X_B(k)]^2\}_{\max,B2}} \quad (17b)$$

$$\vdots$$

$$\hat{S}_{BN}(k) = \frac{\{[X_A(k)E_B(k) - E_A(k)X_B(k)][X_A(k)Y_B(k) - Y_A(k)X_B(k)]^*\}_{BN}}{\{[X_A(k)Y_B(k)]^2 + [Y_A(k)X_B(k)]^2\}_{\max,BN}} \quad (17c)$$

where B stands for "band" and N indicates the Nth band containing the Nth sinusoid. This frequency dependent scaling is necessary when a non-delta function impulse response is used in the control filter. An impulse in the control filter will evenly weight the various reference signal frequency components. When the two data sets are based on an impulse in the control filter only the maximum scalar value is necessary Eq. (15) of the whole spectrum to yield the correctly proportioned secondary path model. However, once the LMS algorithm begins to update the control filter coefficients, the impulse response of the control filter ceases to look impulsive. In fact, for adaptive control of periodic signals the shape of the impulse response normally looks like whatever signal is in the system. As the secondary path changes or as the frequencies in the reference signal change or both, the various reference signal frequency components will be filtered by the coefficients already in the control filter and thus weight each of the frequency components according to the filter. This is why the subband scaling is necessary. Determining where to divide up the subbands is a matter of spectral peak recognition, a tool that has been studied and used extensively in areas such as condition-based maintenance and speech recognition.

Figure 5:
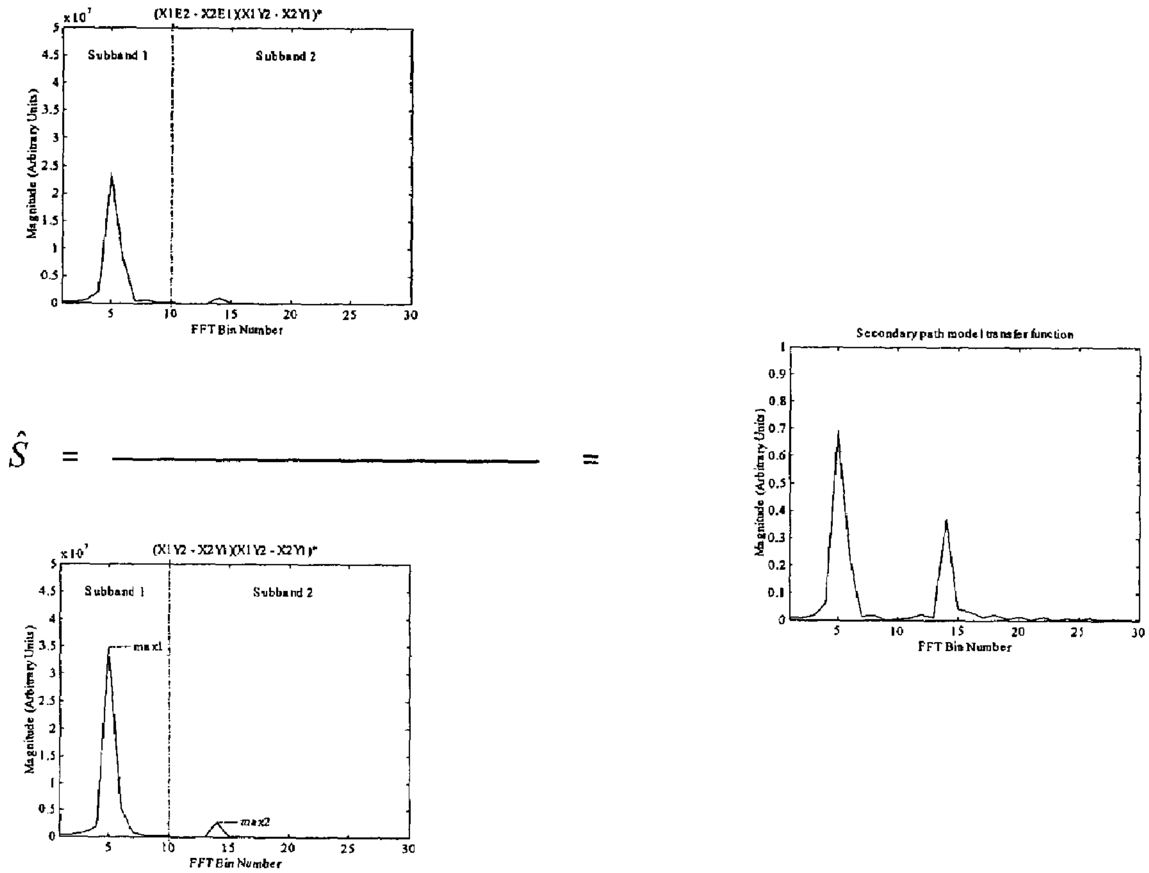
FIG. 5 is a visual representation of Eq. (17) for a two-frequency signal.

A visual representation of the subband scaling methodology is given in FIG. 5. The spectral 'fraction' depicted in FIG. 5 represents Eq. (17) for a two-frequency signal. Here the sampling rate is still 24 kHz. The signal is composed of frequencies at 201 Hz, as before, and 601 Hz with the latter having an amplitude that is half of the former. The frequency spectrum is divided at the midpoint between the two peaks, in this case at bin 10. Subband 1 contains the 201 Hz portion while subband 2 contains the 601 Hz portion of the signal. "max1" in the denominator indicates the maximum scalar value in subband 1. All the bins in the numerator comprising subband 1 are scaled by max1. Subband 2 is handled similarly where "max2" corresponds to the maximum scalar value in subband 2. The resulting secondary path model transfer function is given in FIG. 5 as well. Note the magnitude of the 601 Hz peak relative to the 201 Hz peak—it is roughly half.

There are a couple minor restrictions to this formulation. First, there must exist signals in the system, i.e., the reference, output, and error signals, for the formulation to work. Second, the two error signals can not be zero since this would give the trivial solution for $\hat{P}$ and $\hat{S}$. If the control filter is set to update after each update of the proposed secondary path modeler, then the two error signals could never be zero simultaneously since the second set of data is obtained after the control output has been perturbed. However, since an error signal of zero is usually the target for active noise control systems, this problem is alleviated by setting a threshold below which $\hat{S}$ (or $\hat{P}$) is updated no longer.

Evaluating the Expression

Careful considerations must be made when using Eq. (15) especially with regards to spectral multiplies. This difficulty was encountered in above where the update equation for the filtered-X LMS contains two spectral multiplies corresponding to a linear correlation and a linear convolution in the time domain. Eq. (15) involves seven spectral multiplies each of which correspond to a linear correlation or convolution. Strict bookkeeping is necessary to evaluate the expression correctly. It was explained that the frequency domain filtered-X LMS algorithm requires a secondary path impulse response estimate with length 2L where L is the length of the control filter.

A total of 12L data points are required to calculate the estimate (8L points for one set and 4L points for the second set). This amounts to $(12L)f_s^{-1}$ seconds where $f_s$ is the sampling rate. Since the data acquisition unit must wait for the system to achieve steady state after the coefficients have been adjusted following the acquisition of the first set of data, this adds additional time. The system transients must be allowed to die out before subsequent measurements can be taken. In other words, data that does not reflect the change imposed on the system should not be used. This also applies to the control filter updates. This minimum "waiting period" happens to equal the propagation delay between the control source and the error sensor, or $\tau_{pd}$ where 'pd' stands for propagation delay. This gives a minimum time requirement for the proposed method of $$\tau_{\min} = \frac{12L}{f_s} + \tau_{pd}. \quad (6.4.1)$$

Because the two-equation, two-unknown formulation assumes that the unknowns, P and S, are unchanging during the acquisition of data, the system can not undergo any change during this minimum time, $\tau_{min}$. The filter length and the sampling rate must be set according to the system that is to be controlled.

The beauty of this secondary path modeling method lies in its simplicity and unprecedented accuracy of the resulting secondary path estimate. Again, only the observables, or readily obtained values, namely the reference signal x(n), the output signal y(n), and the error signal e(n), are sufficient for the calculation of the secondary path estimate. No extraneous noise need be injected for the purpose of system identification. This technique is wholly noninvasive.

Description of Experimental Apparatus

The experimental apparatus used to test the real-time implementation of the linear independence method for secondary path modeling can logically be broken down into two parts: the controller used to determine the secondary path model and subsequently the optimal control signal; and the system to which the control is applied. Of particular note in this test is the latter, the system to which the control is applied and tested, which was conceived to give the user ultimate control over the variables that would normally be ungovernable in a 'real' system. This test bed is somewhat unprecedented and allows for a thorough investigation of the validity of any control algorithm. One of the key features besides providing a non-acoustic, thus quiet, method of testing is the "interchangeable" secondary path.

The Controller

The DSP hardware is comprised of a Spectrum DSP32C system board based on the WE® DSP32C digital signal processing chip. Operating from a 50 MHz clock, the DSP chip is capable of executing 12.5 million instructions per second, and can perform up to 25 million floating-point operations per second. It has two high-speed (up to 200 kHz), high-precision (16-bit) analog I/O channels onboard (2 inputs and 2 outputs). A ±3 V analog input range provides full scale operation of the A/D converters (ADC). Similarly, the output range of the D/A converters (DAC) is ±3 V. The two inputs read the reference signal and error signal while one of the outputs is utilized for the control signal output.

The setup of the signal processing system is unconventional in that the signal processing tasks are divided among the aforementioned DSP hardware and the PC in which it operates. The DSP board performs the filtering in the time domain on the input x(n) producing an output y(n) and stores the data, {x(n),e(n),y(n)}, in a circular buffer where e(n) is the error signal. The PC meanwhile downloads the data from the buffer, uses the data to determine the filter coefficients, and uploads the new filter weights to the DSP board. This was done for several reasons. In light of the vintage nature of the DSP board (circa 1989), the relatively low computing power of the DSP chip coupled with its inefficient C compiler necessitated assembly code programming. The tedious nature of assembly code writing would be greatly disadvantageous when writing, testing, and rewriting algorithms. Exploiting the computing power in current PC desktops, the computation tasks of the upper levels of the algorithm were allocated to the PC where the ease of C/C++ programming can also be exploited.

The DSP board was optimized to run a 128-tap filter (128 coefficients) at 24 kHz. To minimize noise and avoid aliasing on the input, the cutoff frequency (−3 dB) of the input filters was set at approximately 9 kHz. Likewise, the cutoff frequency for the output filters was set at 9 kHz to provide a smoothing of the otherwise stepped DAC output signal. The computer used for real-time implementation is an Intel Pentium based PC operating at 200 MHz. Microsoft's Visual C/C++ v6.0 was utilized for the necessary programming to operate the DSP board and calculate and upload to the DSP board the filter coefficients.

The Test Bed

Figure 6:
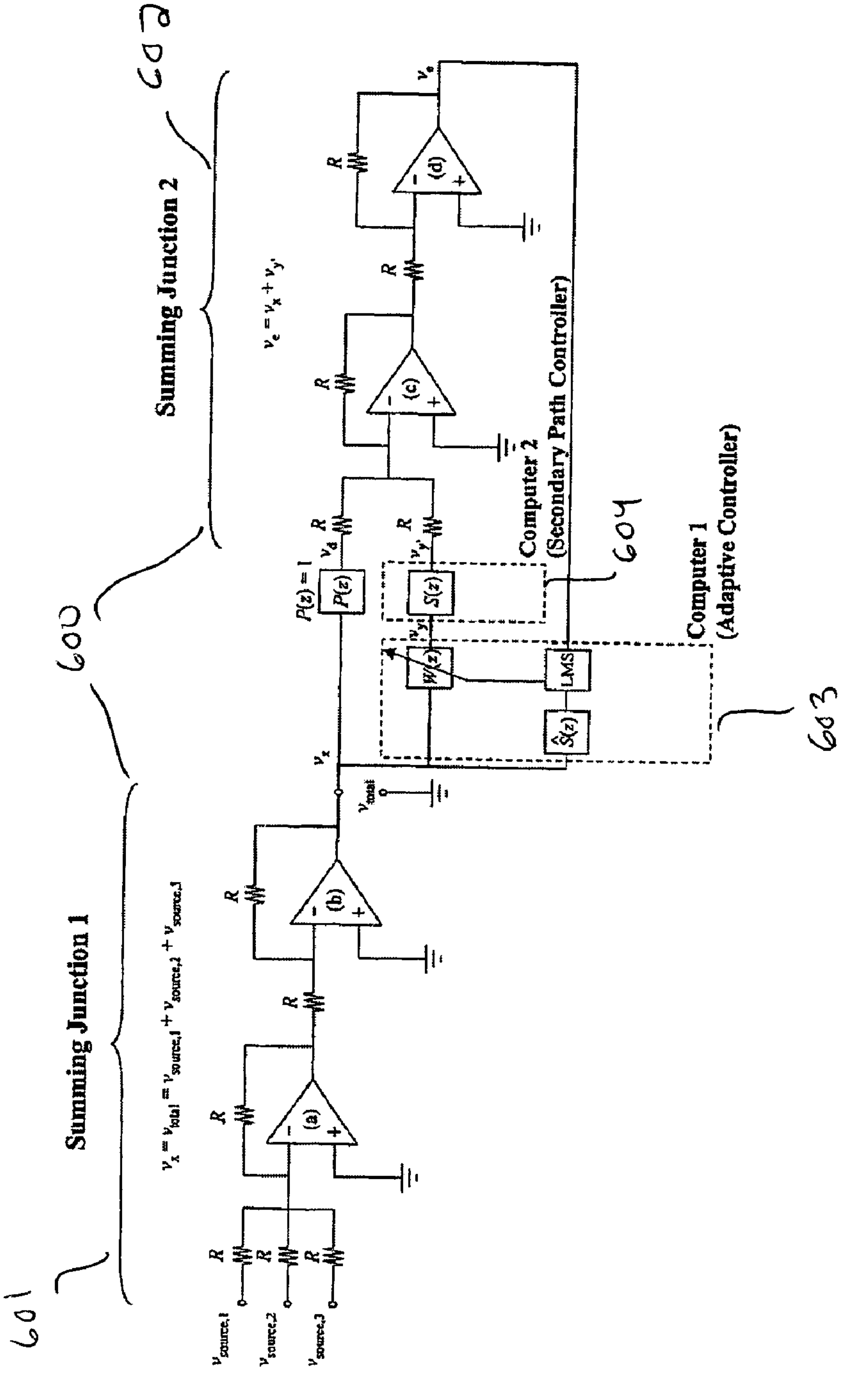
FIG. 6 is an active control system with secondary path interchangeability for testing of the performance of an active control method of the present invention in time-varying environments.

For the purposes of this invention, to eschew the near infinite number of variables that exist in these real systems, a wholly electrical-based test bed was devised for which essentially all parameters are known and where all variables within practicality are accountable to ensure that the performance of the control system, especially the system identification portion, is predictable, reliable, and, most importantly, valid. An electrical circuit performing summing duties, in conjunction with a DSP-capable computer that controls the secondary path transfer function, was designed and assembled to simulate the 'acoustic' or 'vibrational' noise system. Secondary source feedback into the reference signal is avoided in this virtual test bed. The schematic is given in FIG. 6.

Each summing junction 600 is made up of two op amps. Op amps (a) and (c) are evenly weighted summers (with inverted outputs), while op amps (b) and (d) are inverting amplifiers with unity gain whose purpose is to reverse the inversion of the weighted summer. The function of Summing Junction 1 601 is to create multiple sinusoid test signals using multiple signal generators. Although three inputs are pictured, a single signal generator can be used in this configuration (just using one input) and there is no limit to the number of signal generators that can be added. The function of Summing Junction 2 602 is to provide an interference point between the desired signal and the secondary source signal as would be seen by an error sensor in an acoustic or vibrational system. These summing junctions 600 exhibited delays in the output relative to the input (inherent in the feedback configuration) but the delays were largely negligible with respect to the sampling rate.

Computer 1 603 houses the active noise controller which operates on various secondary path modeling filtered-X algorithms including the linear independence method. Computer 2 604 provides a manually adjustable filter that is used to change the phase and amplitude gain of the secondary path to force a change in the secondary path model. The filter in Computer 2 604 is the same filter used in Computer 1 603, running a 128-tap filter at 24 kHz. However, the filter coefficients can be changed via keyboard through a user interface.

The op amps used in this test bed were those embedded in the Analog Devices OP-497 IC chip, a precision picoampere input current quad operational amplifier. It is an 'audio-quality' op amp which provides sufficient bandwidth for the task at hand, where the upper frequency limit for a typical digital feedforward active controller is one third the sampling frequency, or in this case one third of 24 kHz, or 8 kHz. The resistor values indicated by R in the schematic are a nominal 10 kΩ.

Besides providing a 'quiet' environment for the user and for those within the vicinity of the active control system (especially when algorithms fail to converge and diverge), the circuit allows for a 'clean' and well understood environment for the adaptive controller and user. Variables such as gains and frequency responses associated with transducers, power amps, preamplifiers are virtually eliminated along with the delays due to the path between the secondary source output and error sensor. If any variable is not eliminated, it can most likely be accounted for. A system like this is easily simulated in MATLAB or like program, and thus allows for the verification of real-time test results. The most important attribute of this test bed its repeatability. This is vital when comparing behaviors of different algorithms.

The Interchangeable Secondary Path

Figure 7:
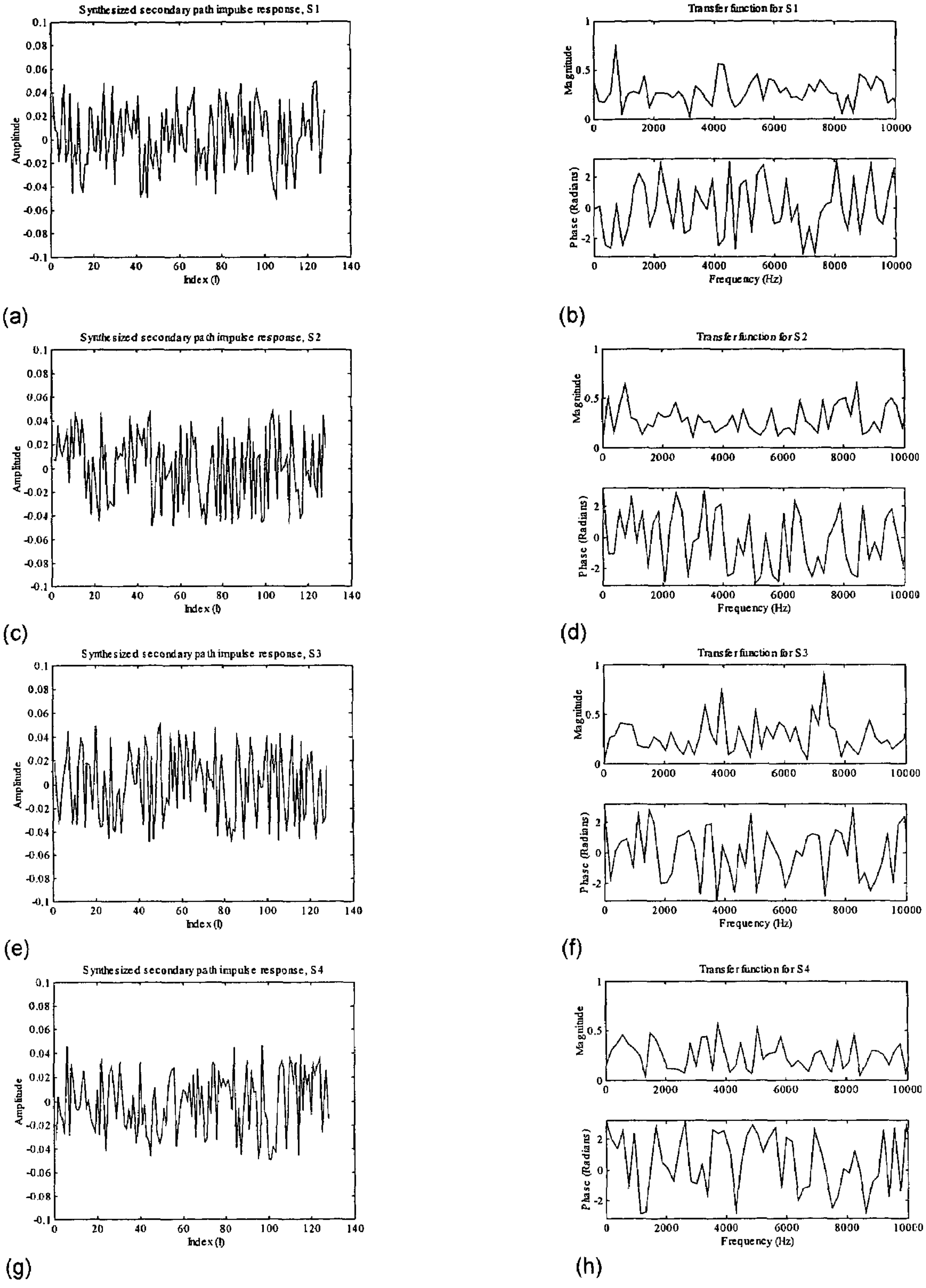
FIG. 7 is impulse responses and corresponding transfer functions for the first four interchangeable secondary paths, S1-S4, for use by Computer 2.
Figure 8:
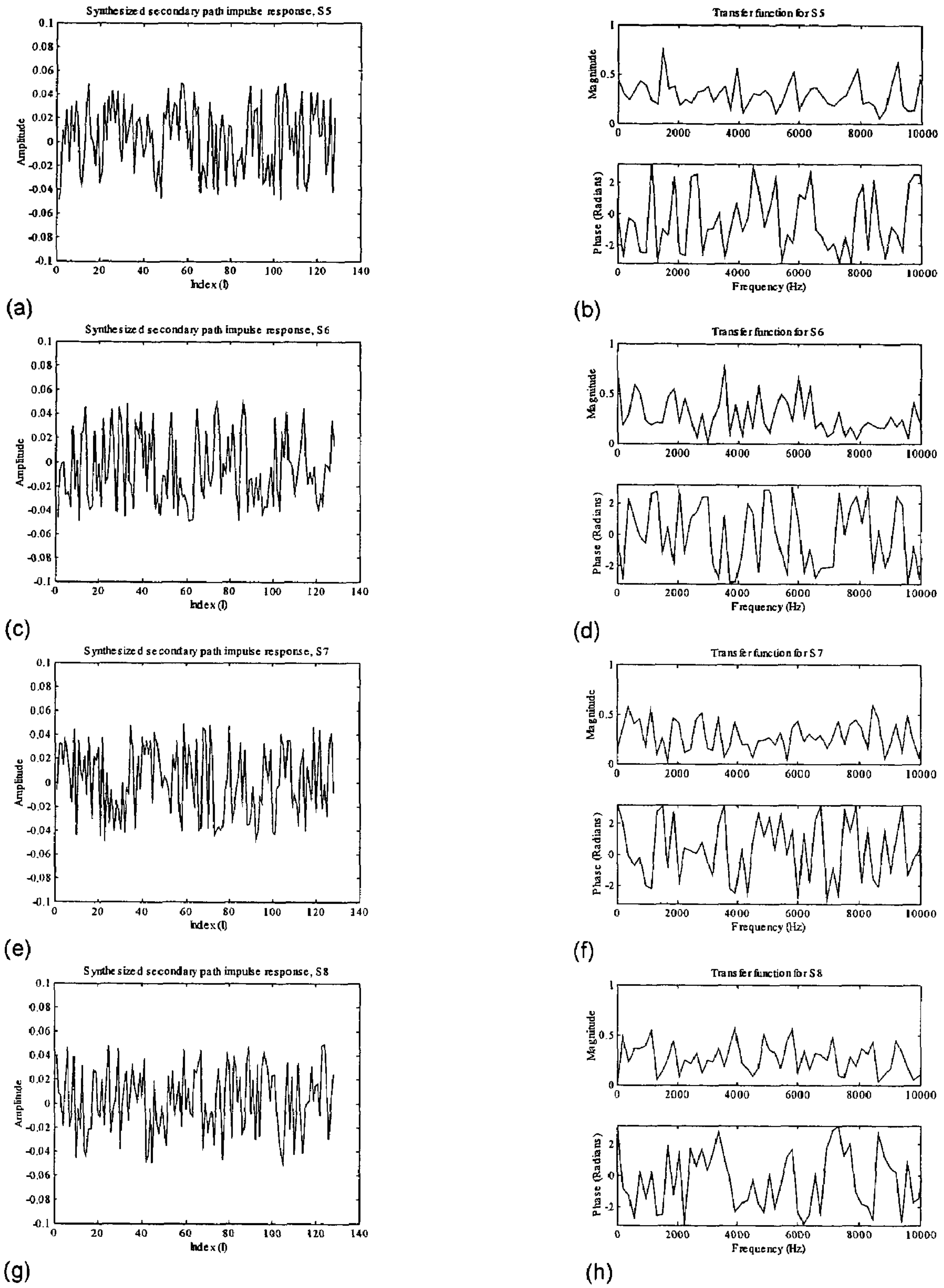
FIG. 8 is impulse responses and corresponding transfer functions for the second four interchangeable secondary paths, S5-S8, for use by Computer 2.

To provide a secondary path that is something more interesting than a mere delay and unity gain, eight sets of random numbers ranging from −0.05 to 0.05 were generated for the impulse responses and saved in text files to be used by Computer 2. These synthesized secondary paths were named S1, S2, . . . S7, and S8 where 'S' stands for 'secondary' and are pictured in FIG. 7 and FIG. 8 along with their transfer functions (magnitude and phase). FIG. 7 shows impulse responses and corresponding transfer functions for first four interchangeable secondary paths, S1-S4, for use by Computer 2. FIG. 8 shows impulse responses and corresponding transfer functions for second four interchangeable secondary paths, S5-S8, for use by Computer 2. While random number-type impulse responses do not necessarily represent transfer functions found in real active noise control systems, they do provide frequency dependent gain and phase.

In this configuration, it is feasible to use impulse responses derived from transfer functions that have been measured in real systems, a feature similar to that seen in modern audio preamps and receivers that incorporate selectable sound fields based on measurements of real concert halls and movie theaters. This is a test method that can provide a cheaper alternative for testing active noise control algorithms.

Finding the Correct Secondary Path Estimate

Figure 9:
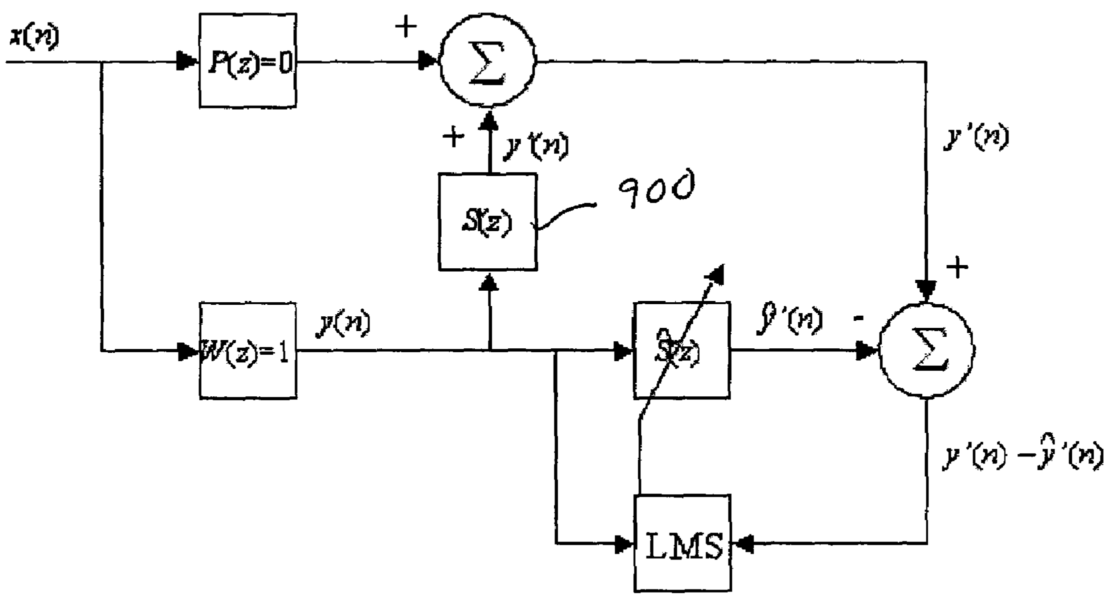
FIG. 9 is a block diagram of an off-line secondary path modeler for secondary path estimate comparison.

Because the objective is to investigate the accuracy of the secondary path models obtained using the method of the present invention, and thus the validity of the secondary path modeler, the estimates obtained must be compared to the correct models. An adaptive filter was programmed on Computer 1 (from FIG. 6) according to the block diagram found in FIG. 9 to perform system identification that would provide the correct estimate for comparison purposes. FIG. 9 shows a block diagram of an off-line secondary path modeler for a secondary path estimate comparison. This is a simple LMS-based adaptive filter that estimates the secondary path in an off-line fashion, i.e. primary noise is made quiet by a simple disconnect in the circuit. S(z) 900 is a filter of length 256 since that is the length required of the frequency domain filtered-X algorithm for linear convolutions and correlations.

Experimental Results

For linear systems, correct secondary path models will allow the algorithm to converge upon the optimal control filter for, in active noise control applications, cancellation of the primary noise. Therefore, the objective of the experiments described here is to determine the accuracy of the secondary path models in both a steady state and evolving system. Because the secondary path is estimated using the signals already in the system, frequency shifts in these signals as well as transfer function changes in the secondary path constitute a changing system. Both types of changes are imposed to test the performance of the present method.

Naturally, single-frequency control is of initial interest and is thus the first subject of investigation. To validate the formulation of the proposed method for multiple frequency periodic signals, dual-frequency control is reviewed thereafter.

Single-Frequency Control

Demonstration of Proposed Method and Test Procedure

Figure 10:
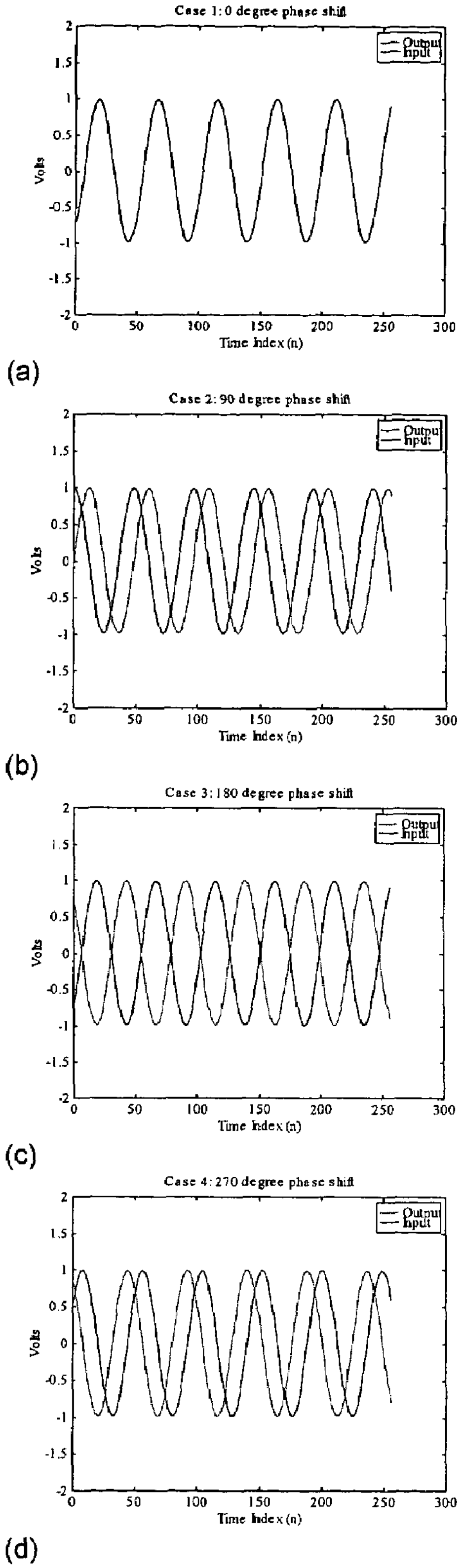
FIG. 10 is input y(n) and output y'(n) of secondary path controller (Computer 2) where delays were imposed to reflect 0°, 90°, 180°, and 270° phase lags.

To demonstrate the proposed method and the testing methodology, a 1 $V_p$ 500 Hz reference signal was considered in four cases. The filter in the secondary path controller was adjusted to give an input, y(n), and an output, y'(n), the relative phases of which were 0°, 90°, 180°, and 270°; the amplitude gain was unity. For the 128-tap filter and 24 kHz sampling rate, this required a unity impulse at $s_0=1$, $S_{12}=1$, $S_{24}=1$, and $S_{36}=1$, respectively (with all other coefficients zeroed), for the S(z) filter. FIG. 10 shows the phase changes at the output of the secondary path controller. FIG. 10 shows input y(n) and output y'(n) of secondary path controller (Computer 2) where delays were imposed to reflect 0°, 90°, 180°, and 270° phase lags.

Figure 11:
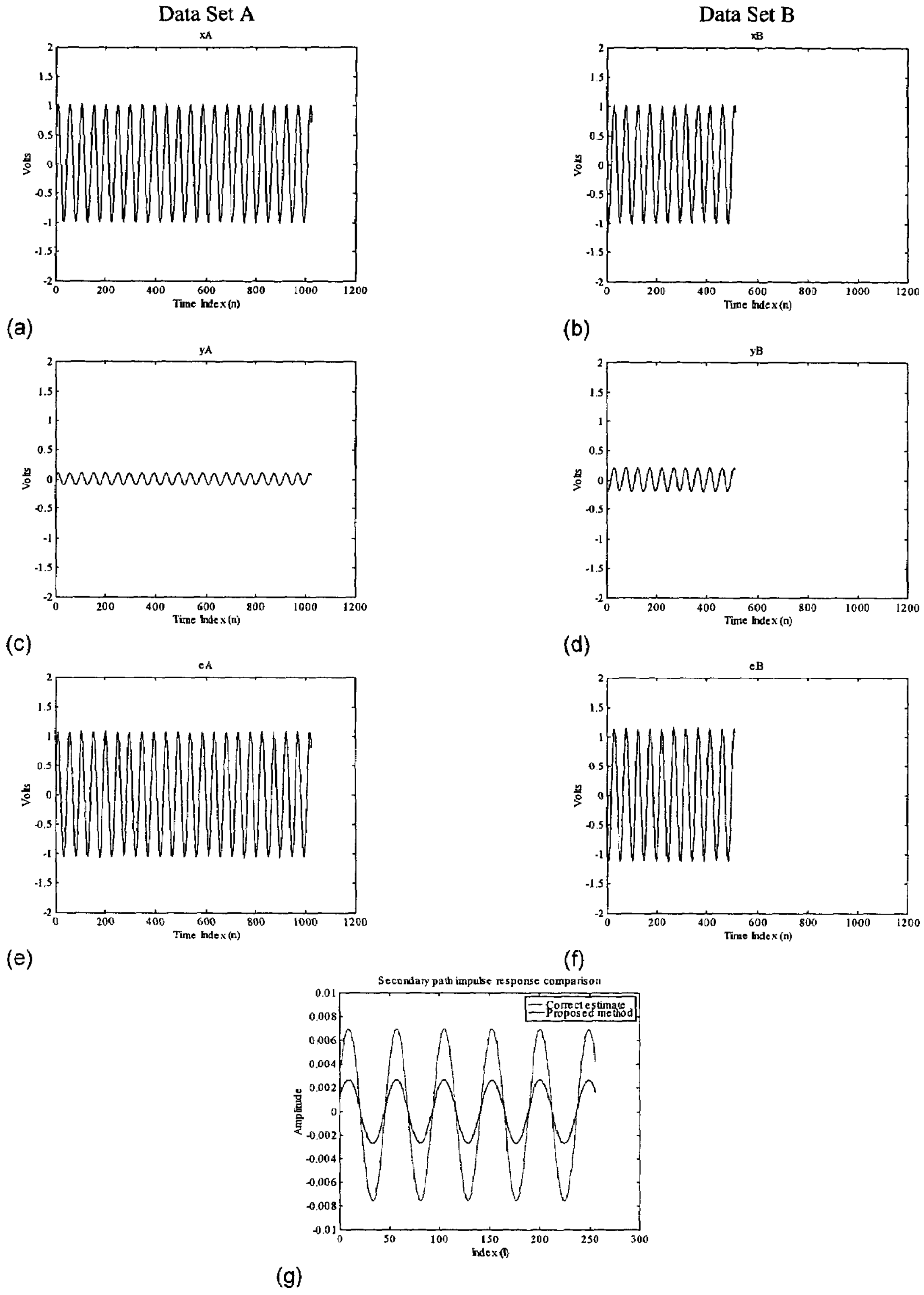
FIG. 11 is data and a resulting secondary path impulse response estimate for case 1.
Figure 12:
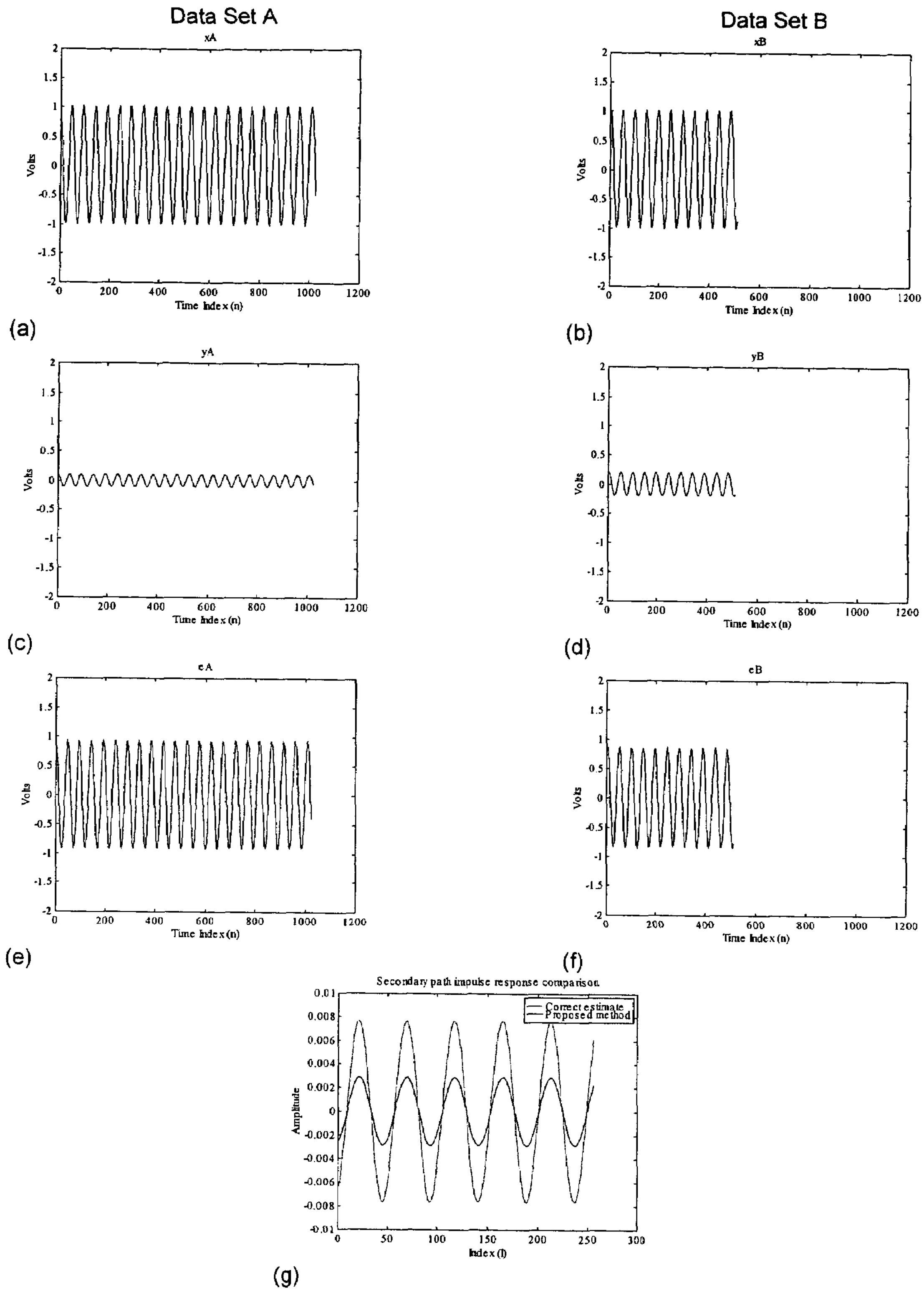
FIG. 12 is data and a resulting secondary path impulse response estimate for case 2.
Figure 13:
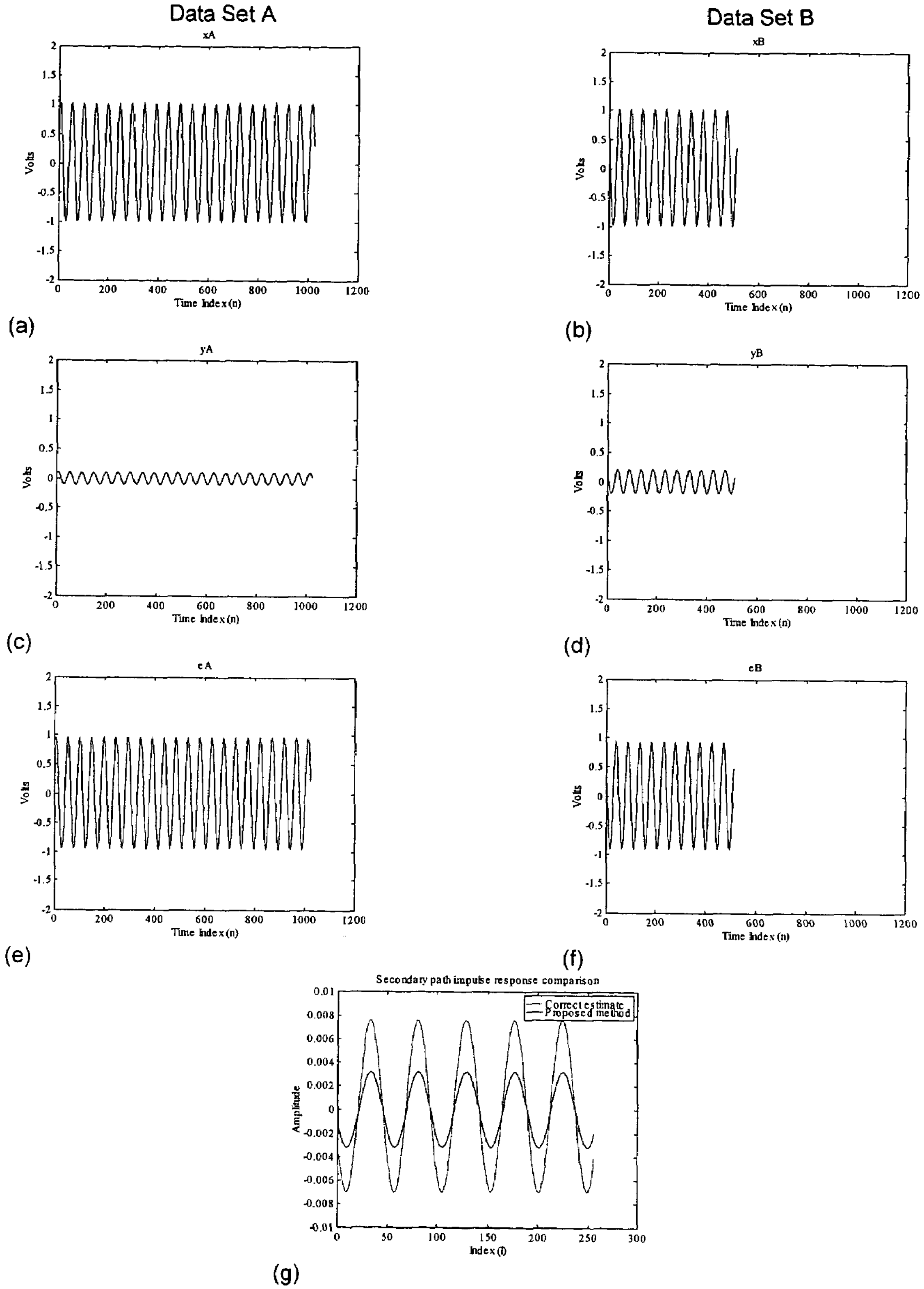
FIG. 13 is data and a resulting secondary path impulse response estimate for case 3.
Figure 14:
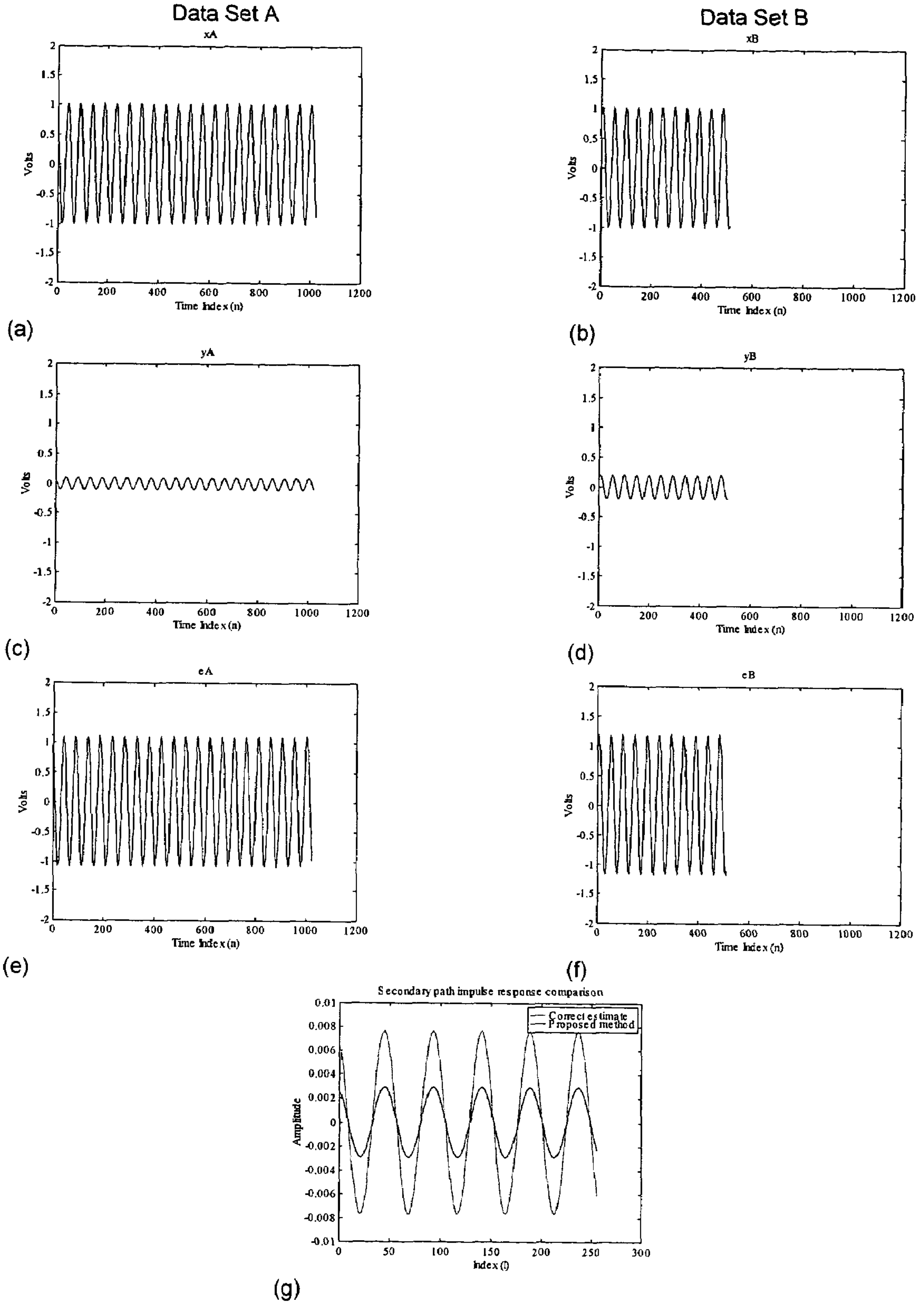
FIG. 14 is data and a resulting secondary path impulse response estimate for case 4.

FIGS. 10 through 14 aid in visualizing the mechanics of the present method of secondary path modeling using each of the aforementioned four cases. FIG. 11 shows data and a resulting secondary path impulse response estimate for case 1; FIG. 12 shows the same for case 2, FIG. 13 for case 3, and FIG. 14 for case 4. In this set of tests, the initial impulse response in the control filter was an impulse of magnitude 0.1 at l=0. This gives for the first data set, Data Set A, an output signal y(n) that is in phase with the input or reference signal x(n) and has an amplitude that is 10% of the amplitude of the input, or 0.1 $V_p$. Superposition of these signals yields the error signal (amplitude is not necessarily 1.1 $V_p$ due to the delays inherent in the DSP hardware described later). Data Set B is derived by doubling the impulse response of the control filter from 0.1 to 0.2 to give an output y(n) that is 20% of the amplitude of the input x(n), or 0.2 $V_p$, but still in phase. This change is reflected in the error signal.

The secondary path model $\hat{S}(z)$ is calculated using the present method, the impulse response of which is shown in subfigure (g) in FIGS. 11 through 14. In these subfigures, the secondary path model is compared to the correct estimate obtained using the LMS-based off-line secondary path estimator. It is readily apparent that the phase of the impulse response derived using the present method is exact. The only discrepancy is the amplitude. For all four cases the amplitude of the present method's impulse response estimate is roughly 40% of the correct estimate. This is perfectly acceptable according to the discussion above. These comparisons are summarized in FIG. 15 to help view the corresponding shifts in phase more readily. The 90° multiple phase shifts imposed by the secondary path controller are evident in these plots; the impulse response shifts in 90° increments from (a) to (d).

Figure 15:
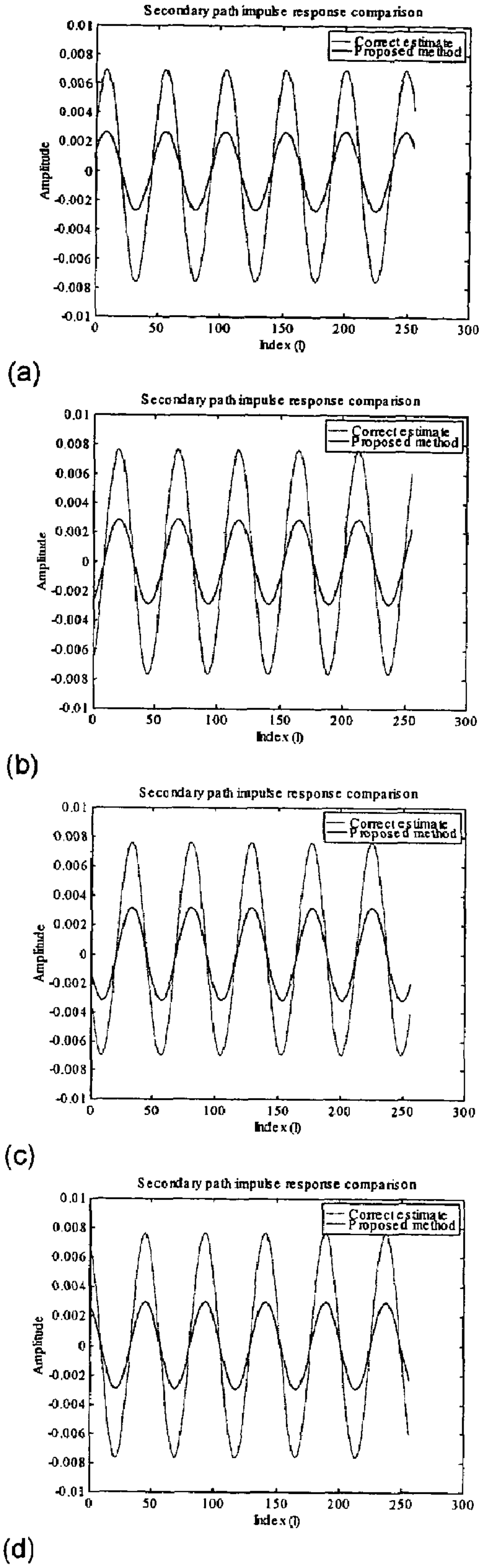
FIG. 15 is a summary of impulse response comparisons for cases 1-4.
Figure 16:
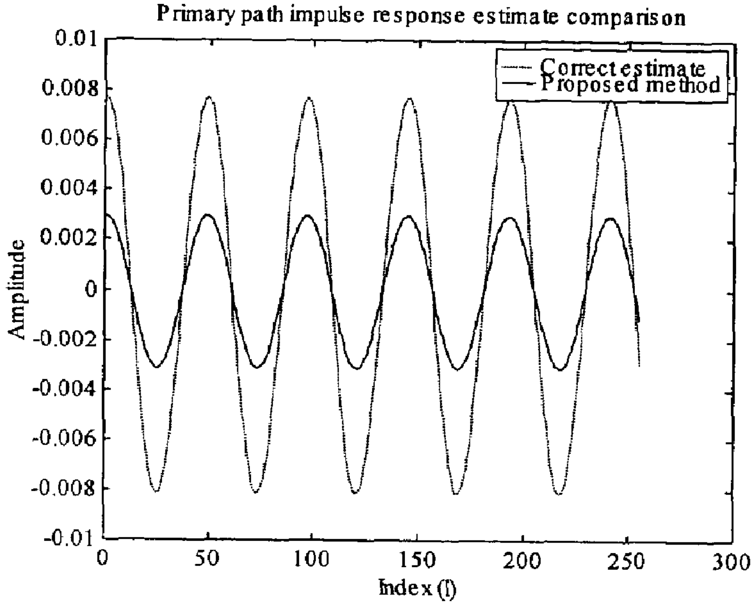
FIG. 16 is primary path and secondary path estimates revealing delay inherent in the secondary path.
Figure 16:
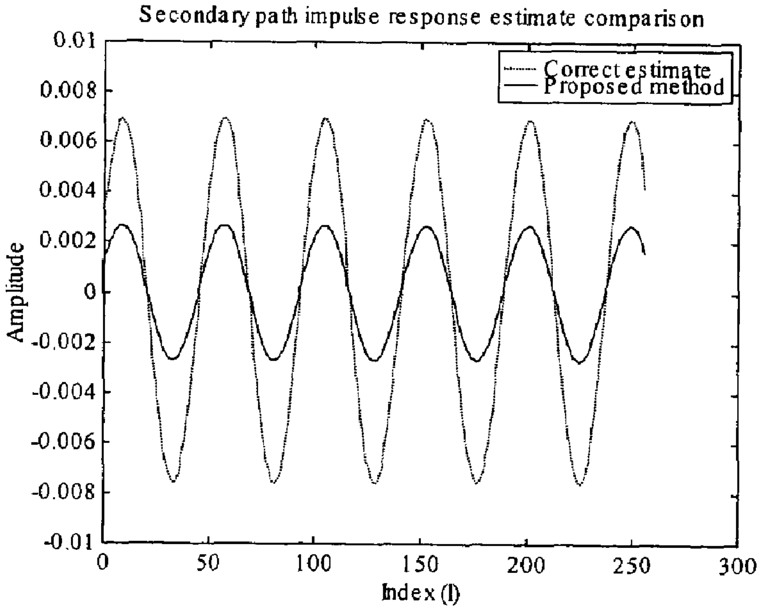

It should be noted that the impulse response estimates in FIG. 15 provide sufficient evidence of a delay that exists in the secondary path of this "virtual test bed". A zero delay path will yield an impulse response seen in (a) of FIG. 16, which depicts the impulse response estimate comparison of the primary path, calculated in the same manner using Equation (6.2.15), where the impulse response begins at its peak amplitude at l=0. The impulse response of the secondary path is shifted nearly 8 samples relative to that of the primary path, a delay amounting to 333 μs for a sampling frequency of 24 kHz. Frequency response measurements of the summing junction (the weighted summer with the inverter) revealed linear phase corresponding to a 9.1 μs delay or 0.22 samples relative to the 24 kHz sampling rate. This implies that the DSP hardware is the primary contributor to this delay. Theoretically, the two DSP cards should only account for 1 delay sample each. However, what is being observed is the combination of delays contributed by the anti-aliasing filters (Sallen-Key 4th order lowpass) at the input, smoothing filters at the output, the A/D converters and D/A converters, sample-and-hold circuits, etc. (the conversion from the analog to digital domain and vice versa is far from instantaneous). Frequency response measurements of each DSP input/output revealed a linear phase response corresponding to a roughly 150 μs delay or 3.8 samples relative to 24 kHz. Fortunately, the filtered-X LMS algorithm compensates for these numerous delays without the need for identifying the causes and examining in detail every one of them.

Nonstationary Secondary Path Performance

The same frequency sinusoid of 500 Hz, 1 $V_p$, was used to test the performance of the present method for an evolving secondary path. The interchangeable secondary path system was introduced above; the synthesized impulse responses were described in detail as well. The procedure was as follows: at system startup, 10% (with respect to amplitude)

of the reference signal input would be leaked into the system at the secondary output (in phase) as was done in the demonstration above. The secondary path modeler would then gather one set of data. Next the control filter would double the amplitude of the secondary output, and the modeler would then collect the second set of data. Using the resulting secondary path model, the adaptive control filter is allowed to update 64 times. The secondary path impulse response is then replaced via Computer 2 with the next synthesized impulse response. For this and subsequent secondary path estimations, the existing control filter weights are multiplied by a constant of 1.1 to achieve linear independence for data sets B with respect to the corresponding data sets A. The secondary path estimate calculation is done once after each change in the secondary path and the estimate is then used by the filtered-X LMS algorithm to update the control filter, again, 64 times.

Figure 17:
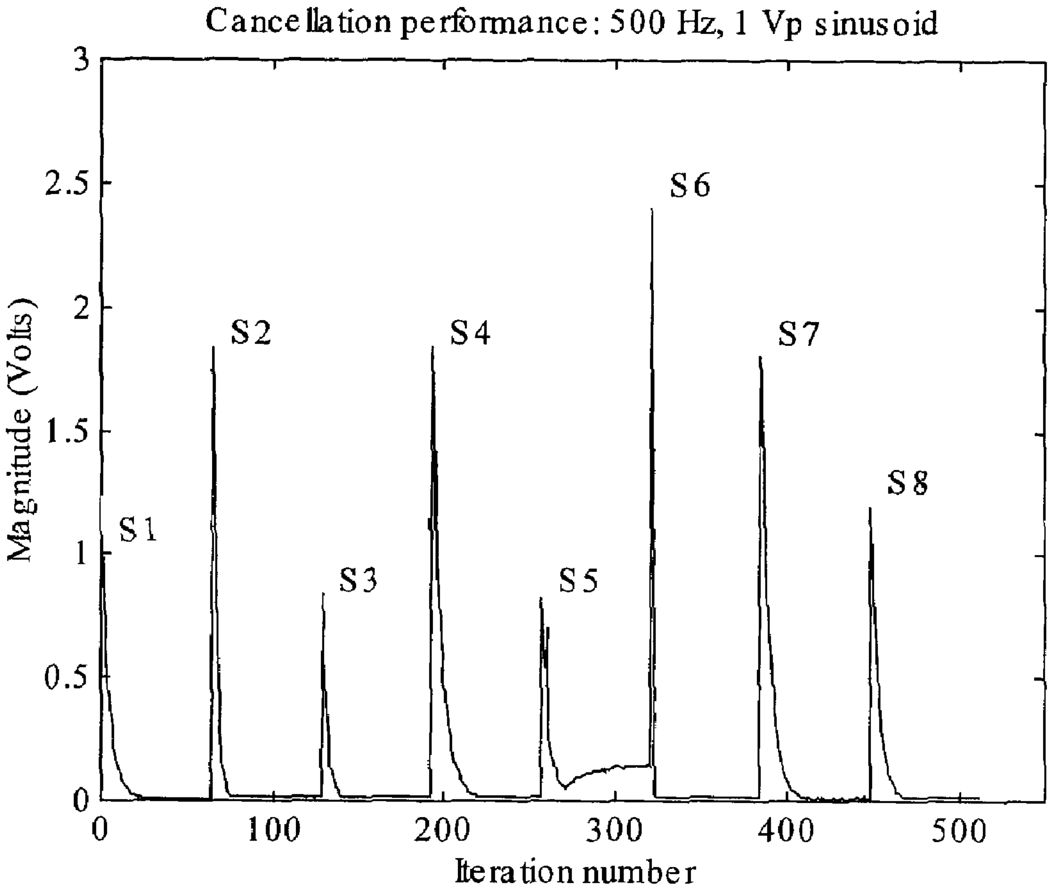
FIG. 17 is the magnitude error signal (initially 1 $V_p$) as the active controller adapts to changes in the secondary path indicated by S1, S2, . . . , S8.
Figure 18:
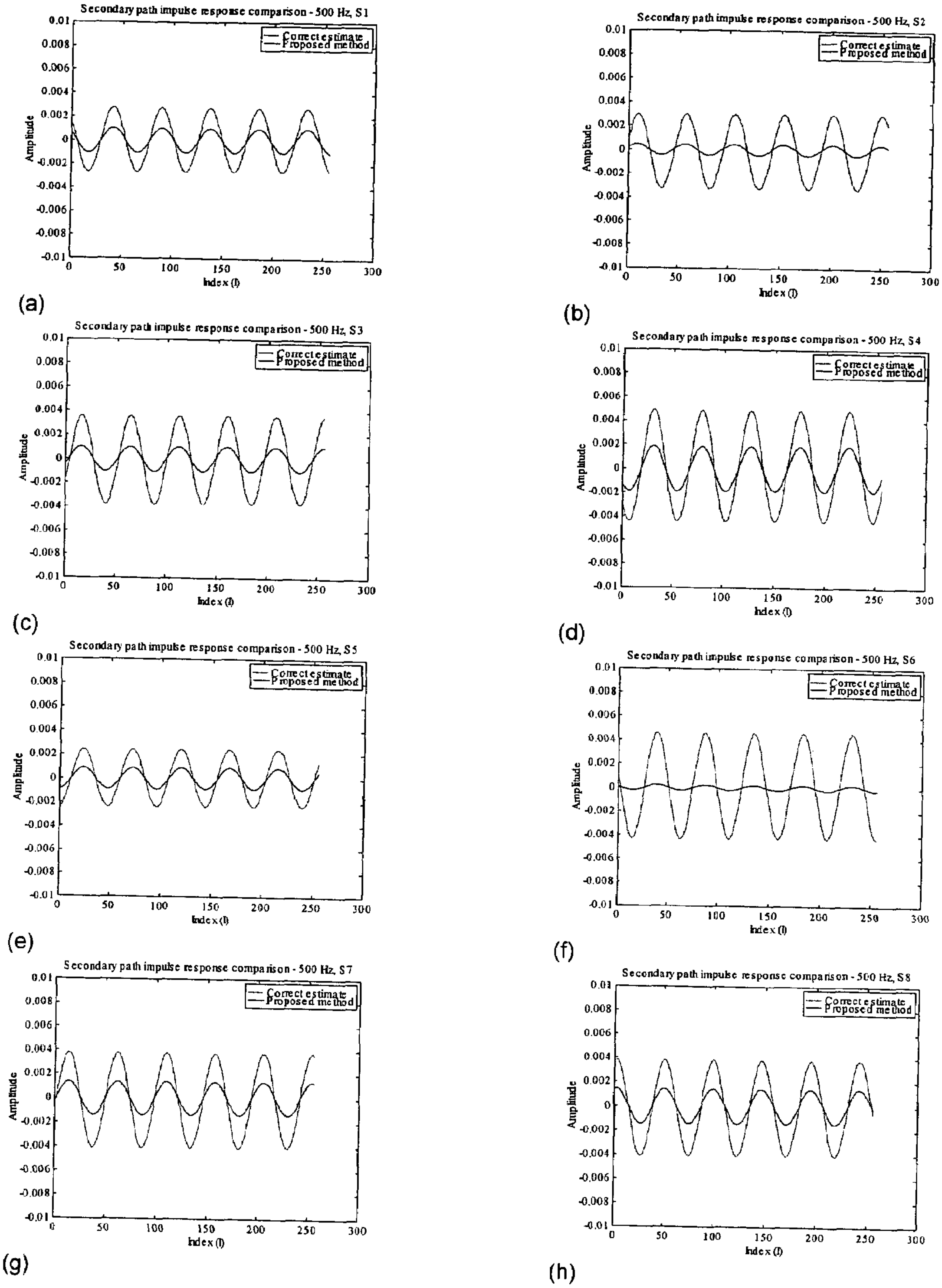
FIG. 18 is a secondary path impulse response estimate comparison for each of the secondary paths, S1-S8, imposed during system operation.

FIG. 17 shows the magnitude of an error signal (initially 1 Vp) as active controller adapts to changes in the secondary path indicated by S1, S1, . . . , S8. The performance of this active noise controller employing the present secondary modeling algorithm for this particular test is revealed in FIG. 17. The amplitude of the error signal is given at each iteration where the amplitude is in volts. It is reduced to roughly in the tens of millivolts range. The amount of dB attenuation is of little concern here since the secondary path modeler is what is under the microscope. Besides, the maximum amount of dB attenuation achievable is dependent on the magnitude of the error signal before control is applied. No instabilities were encountered during this test. This exceptional performance is attributed to the correctness of the secondary path models made evident in FIG. 18 where the impulse response estimates for S(z) are pictured. FIG. 18 shows a secondary path impulse response estimate comparison for each of the secondary paths, S1-S8, imposed during system operation. For each and every change in the secondary path, the secondary path modeler identified the system accurately in phase while consistently being under in magnitude. Because the magnitude is consistently below the correct magnitude, this allows the step size to remain constant without encountering divergence of the filtered-X algorithm. The rate of cancellation is compromised somewhat but stability is assured. This level of accuracy in the secondary path model is unprecedented in a noninvasive system identification noise control algorithm.

Sinusoid of Shifting Frequency

The next investigation involved the shifting of the sinusoid in frequency in a stationary secondary path. Because noninvasive secondary path modelers use signals already in the system to perform system identification at the frequencies contained in the signals, any change in the frequency content will require the modeler to identify the system at the new frequencies. Here the secondary path filter was zeroed except for the first coefficient, $s_0$, which was set to one. As described above, this gives a frequency response with linear phase corresponding to a delay of about 333 μs; the gain is unity. The secondary path modeler is forced to compensate and adjust to the subsequent change in phase of the sinusoid as it shifts in frequency (the frequencies with smaller wavelengths will experience larger phase shifts with the same time delay).

The frequency of the sinusoid was initialized at 500 Hz. The procedure in updating the control filter and secondary path modeler is identical to that for the changing secondary path test described above. The frequency of the sinusoid is shifted up in increments of 100 Hz until it reaches 1 kHz at which point the frequency is shifted up in increments of 1 kHz through 9 kHz. Between each shift 64 adaptations of the control filter are allowed.

Figure 19:
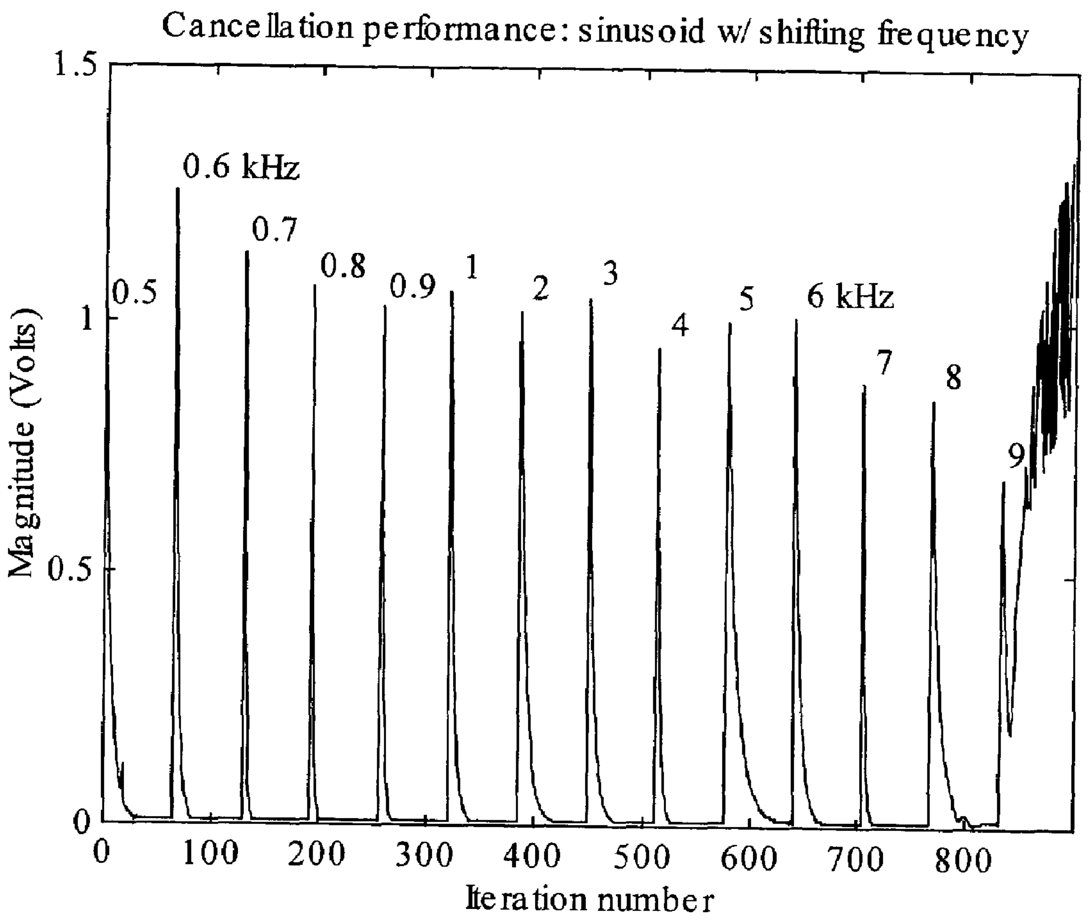
FIG. 19 is a magnitude of error signal (initially 1 $V_p$) as the active controller adapts to changes in frequency of the reference signal in a secondary path environment.
Figure 20:
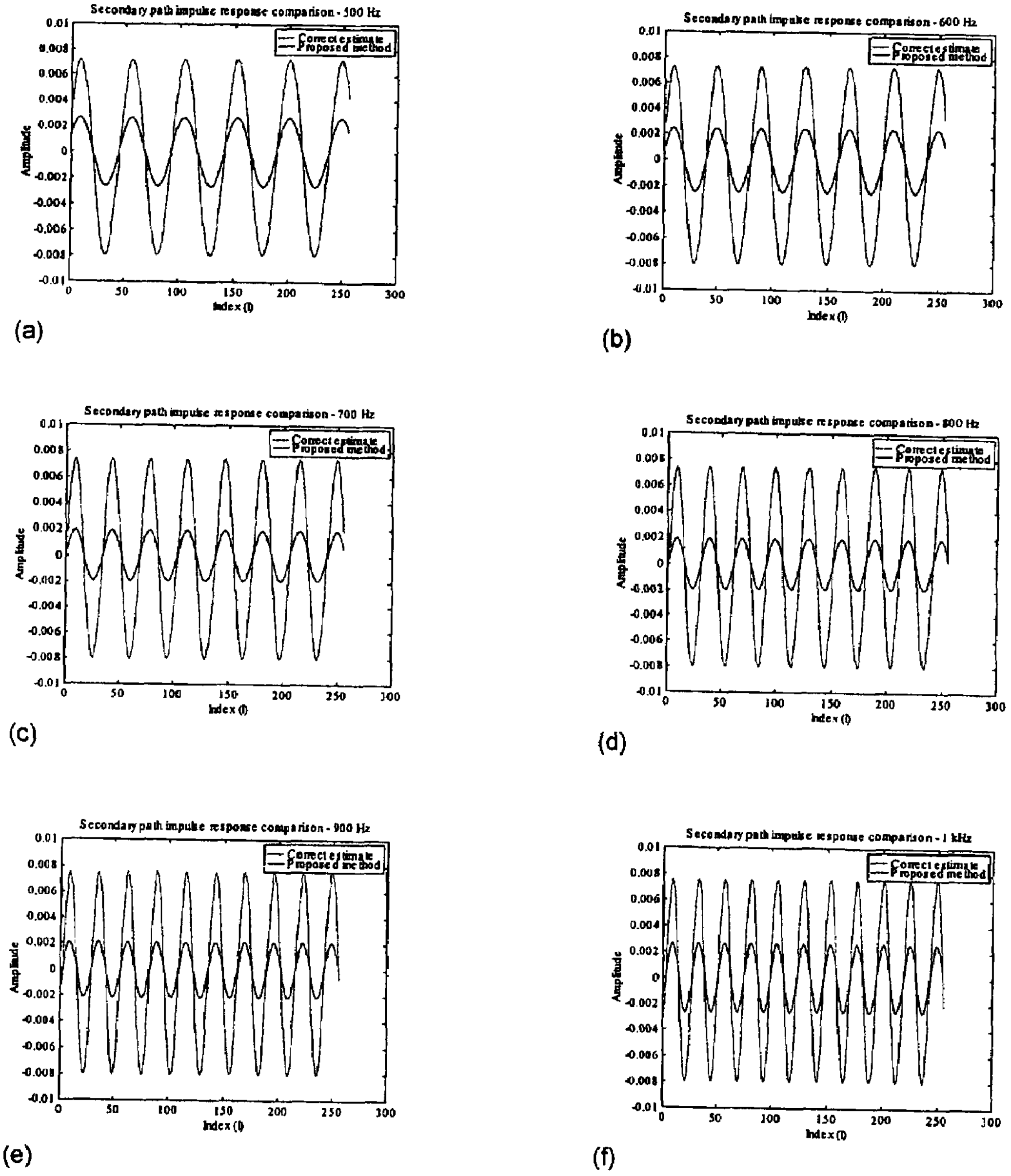
FIG. 20 is a secondary path impulse response estimate comparison for shifting frequency of sinusoid, 500 Hz to 1 kHz in 100 Hz increments, during operation of a system of the present invention.
Figure 21:
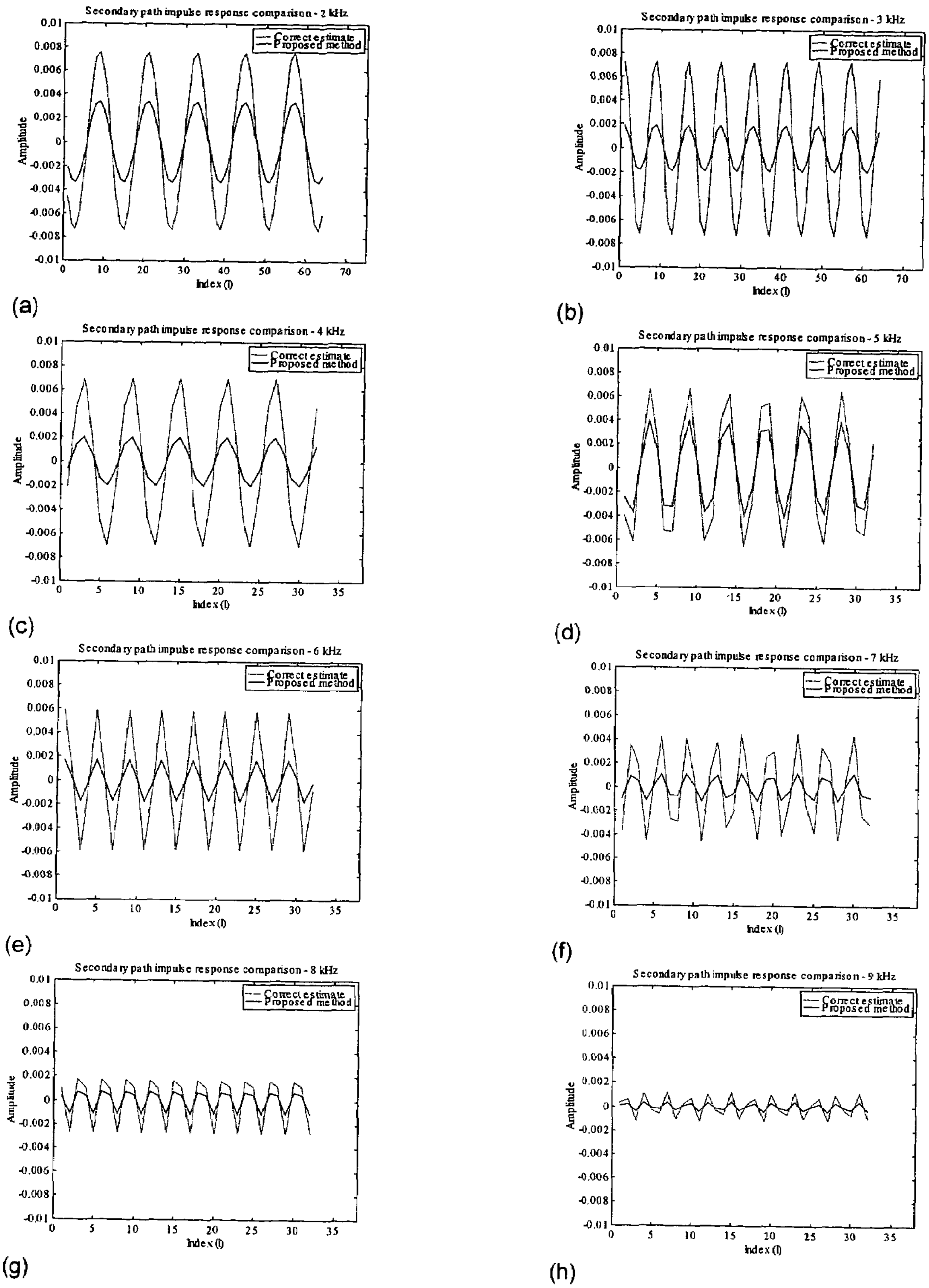
FIG. 21 is a secondary path impulse response estimate comparison for shifting frequency of sinusoid, 2 kHz to 9 kHz in 1 kHz increments, during operation of a system of the present invention.

The performance of this algorithm for this test is shown in FIG. 19. FIG. 19 shows a magnitude of an error signal (initially 1 Vp) as active controller adapts to changes in frequency of reference signal in a stationary secondary path environment. The magnitude of the error signal is given at each iteration where the amplitude is in volts. As expected the magnitude of the sinusoid at the start is close to 1 $V_p$, The next figures, FIGS. 20 and 21, reveal the secondary path impulse responses as determined by the proposed method during system operation; these are compared to the correct impulse response estimates. FIG. 20 shows a secondary path impulse response estimate comparison for shifting frequency of sinusoid, 500 Hz to 1 kHz in 100 Hz increments, during system operation. FIG. 21 shows a secondary path impulse response estimate comparison for shifting frequency of sinusoid, 2 kHz to 9 kHz in 1 kHz increments, during system operation. Again, the phases of the impulse responses correspond exactly. The amplitudes of the proposed method's impulse responses are consistently lower than the respective amplitudes of the correct estimates. And, as before, the filtered-X algorithm never went unstable as the frequency shifted. This is attributable to the accuracy of the secondary path estimates.

It is interesting to note the divergence of the control filter at 9 kHz in FIG. 19. Snyder states that active control systems work reasonably well from frequencies approaching $f_s/100$ to frequencies up to $f_s/3$ where $f_s$ is the sampling rate. This would correspond to a range of 240 Hz up to 8 kHz for the 24 kHz sampling rate utilized in this set of tests. The ineffectiveness of the adaptive controller at 9 kHz agrees rather well with Snyder's report.

Multiple-Frequency Control

As was done for single-frequency control, how the present on-line secondary path modeler copes with both the evolving secondary path and the shifting frequencies was investigated for multiple frequency noise signals. Here, only two frequency signals are used since only two are necessary to validate the generalization of the present method's formulation, Eq. (17), for multiple frequencies.

Peak recognition is necessary for secondary path modeling using the present method when multiple-frequency signals are involved in order to determine where to split up the frequency spectrum to create the subbands. However, validation of the present method for multiple frequencies does not necessarily require implementation of peak recognition into the real-time controller. The subbands can be set a priori if the frequencies to be imposed on the system are known. This is in fact what is done here for the two frequency signals.

Nonstationary Secondary Path Performance

Figure 22:
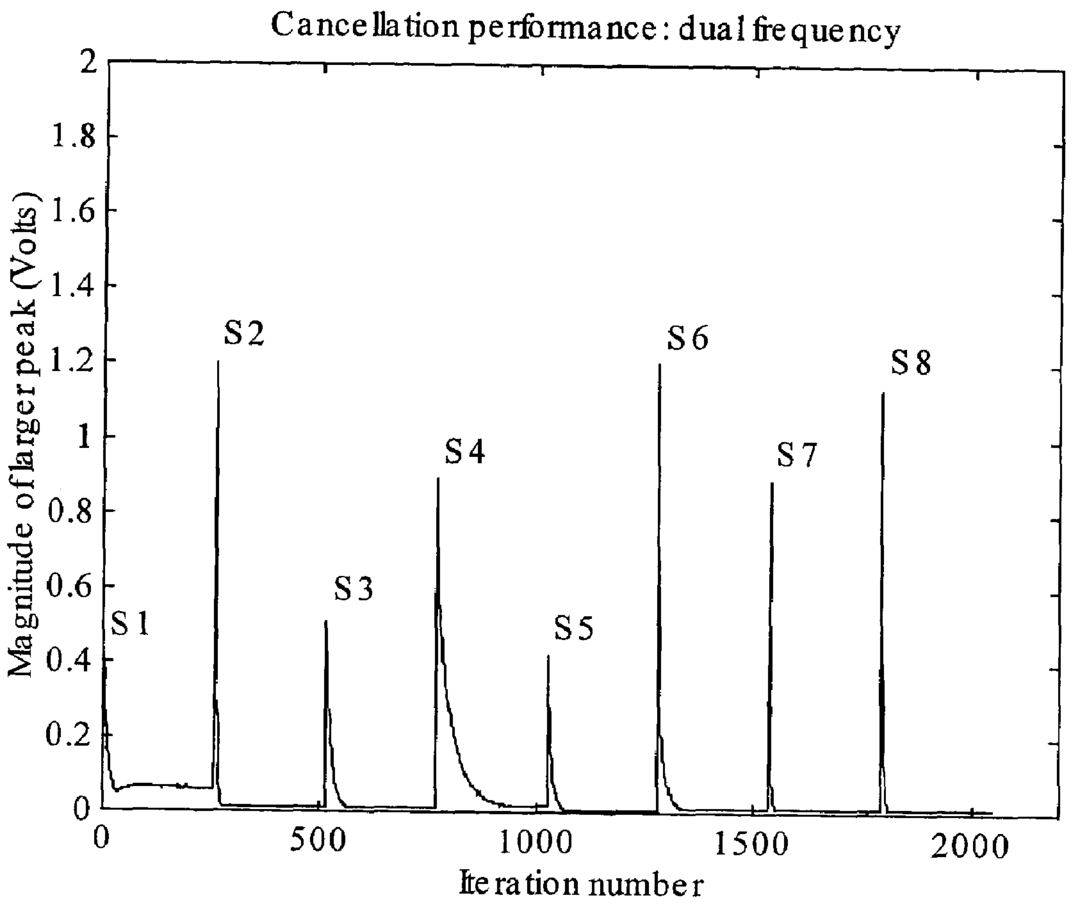
FIG. 22 is a magnitude of the larger of the two sinusoids in error signal as an active controller of the present invention adapts to changes in the secondary path indicated by S1, S2, . . . , S8.
Figure 23:
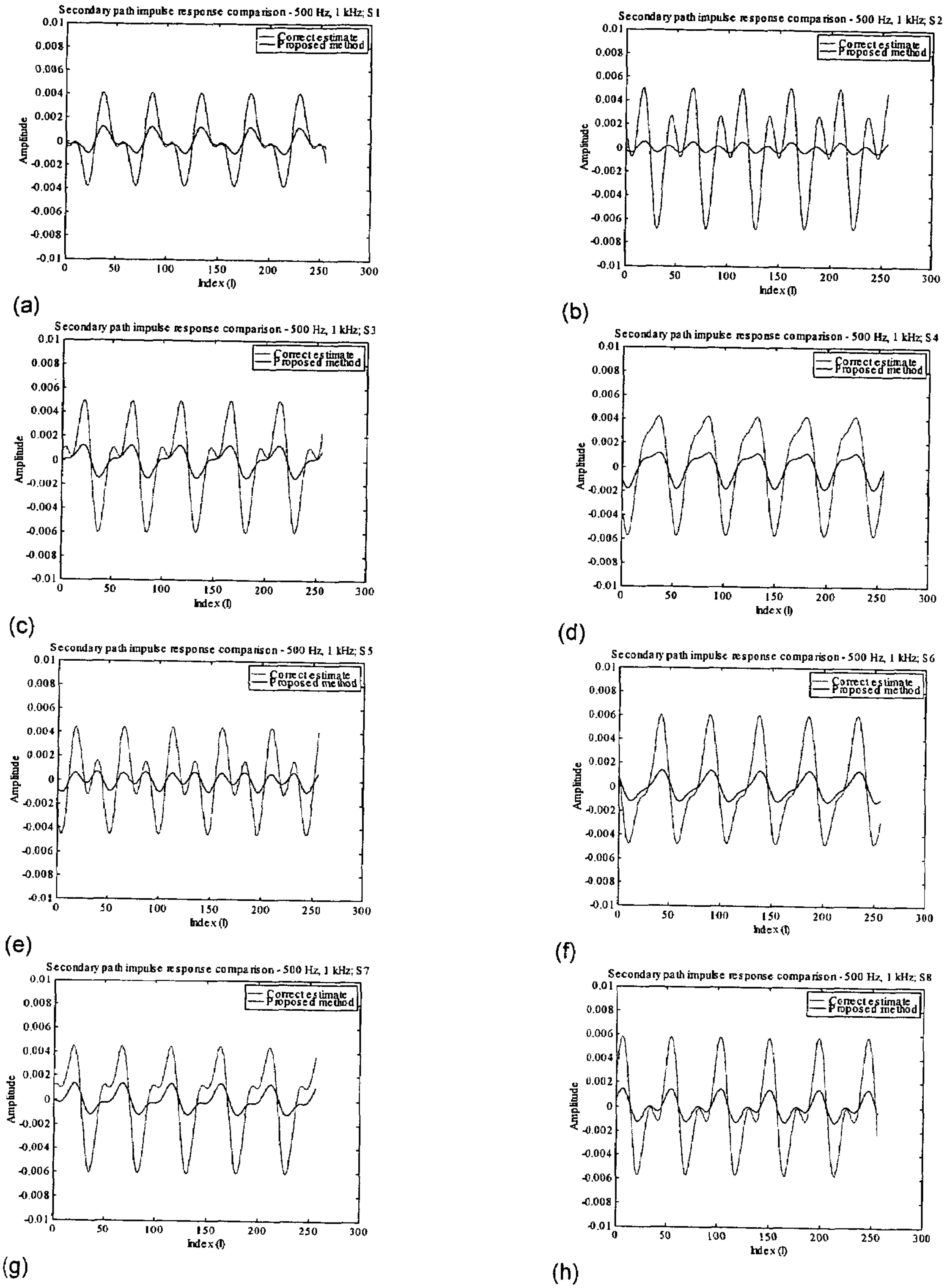
FIG. 23 is a secondary path impulse response estimate comparison for each of the secondary paths, S1-S8, imposed during the operation of a system of the present invention.

The two frequencies used for this test were 500 Hz and 1 kHz, each with amplitude 0.5 $V_p$ to prevent overload of the A/D and D/A converters. The spectrum was divided into two subbands at the midpoint between the two peaks, each accommodating their respective sinusoid. The testing procedure is almost identical to that described above where each of the eight secondary paths, S1-S8, is imposed after a number of iterations. For this test 256 iterations are allowed instead of the previous 64. This was done to give the controller as much time as was necessary to cancel the signal as best it could. Again, no instabilities were encountered during the test. The performance of the active controller is depicted in FIG. 22, which shows the magnitude of the larger of the two sinusoids in error signal as active controller adapts to changes in the secondary path indicated by S1, S1, . . . , S8. The corresponding secondary path impulse response estimates are given in FIG. 23, which shows the secondary path impulse response estimate comparison for each of the secondary paths, S1-S8, imposed during system operation. As was seen for the single frequency control, the phase is exact as is the shape of the waveforms. The magnitude is consistently less than that of the correct estimate—perfectly acceptable for the filtered-X adaptive controller.

Dual-Frequency Signal with Frequency Shifts

The last investigation involves the shifting of the frequencies of the dual-frequency signal in a stationary secondary path. Similar to what was described above the secondary path filter was zeroed except for the first coefficient, $s_0$, which was set to unity. The dual-frequency signal was initialized at 500 Hz and 1.5 kHz, each with amplitude 1 $V_p$, the second being three times the frequency of the first. The upper frequency can be viewed as the third harmonic of the fundamental. This multiple is preserved as the "fundamental" frequency moves up in frequency in increments of 100 Hz up to 1200 Hz (the final frequency corresponds to a third harmonic of 3600 Hz). For this test the adaptive controller is allowed 128 updates in between frequency shifts.

For each frequency shift, the frequency spectrum was divided accordingly at the bin splitting the two peaks. These bin values were determined a priori and used during the test.

Figure 24:
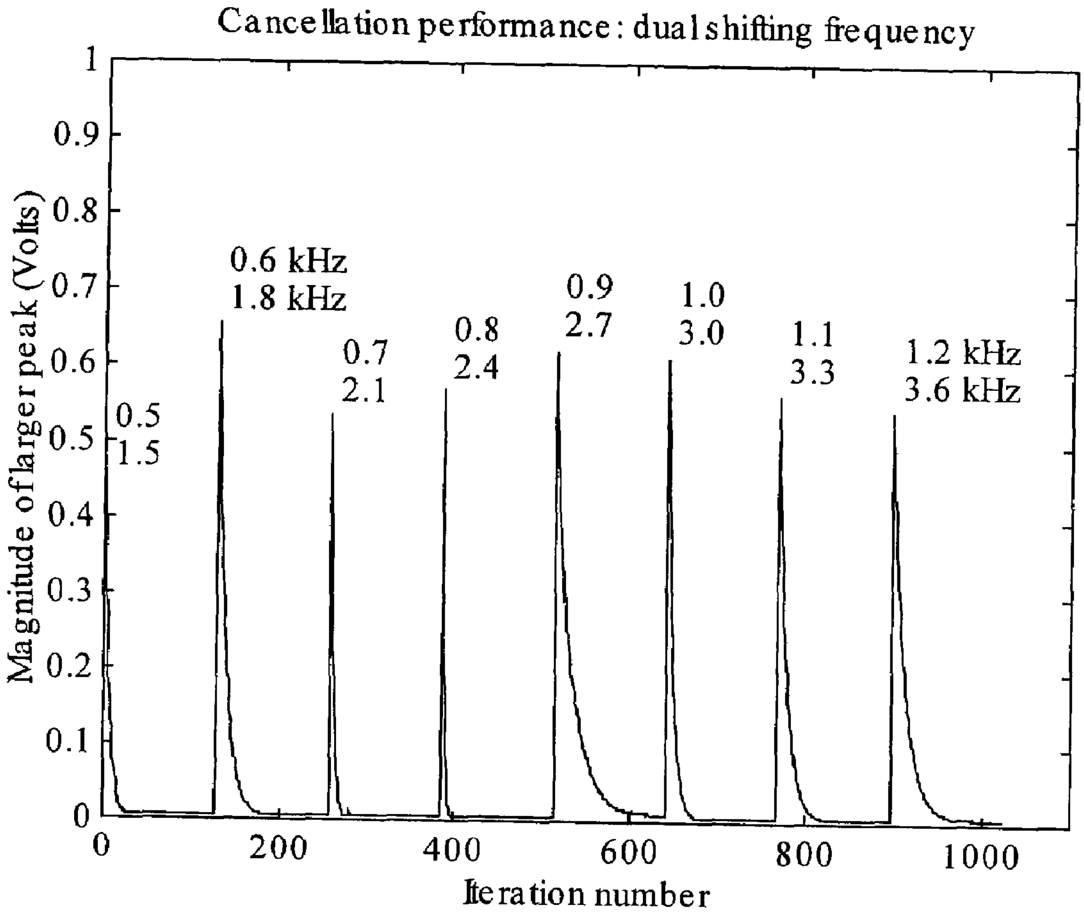
FIG. 24 is a magnitude of the larger of the two sinusoids in error signal as an active controller of the present invention adapts to changes in frequency in a stationary secondary path environment.
Figure 25:
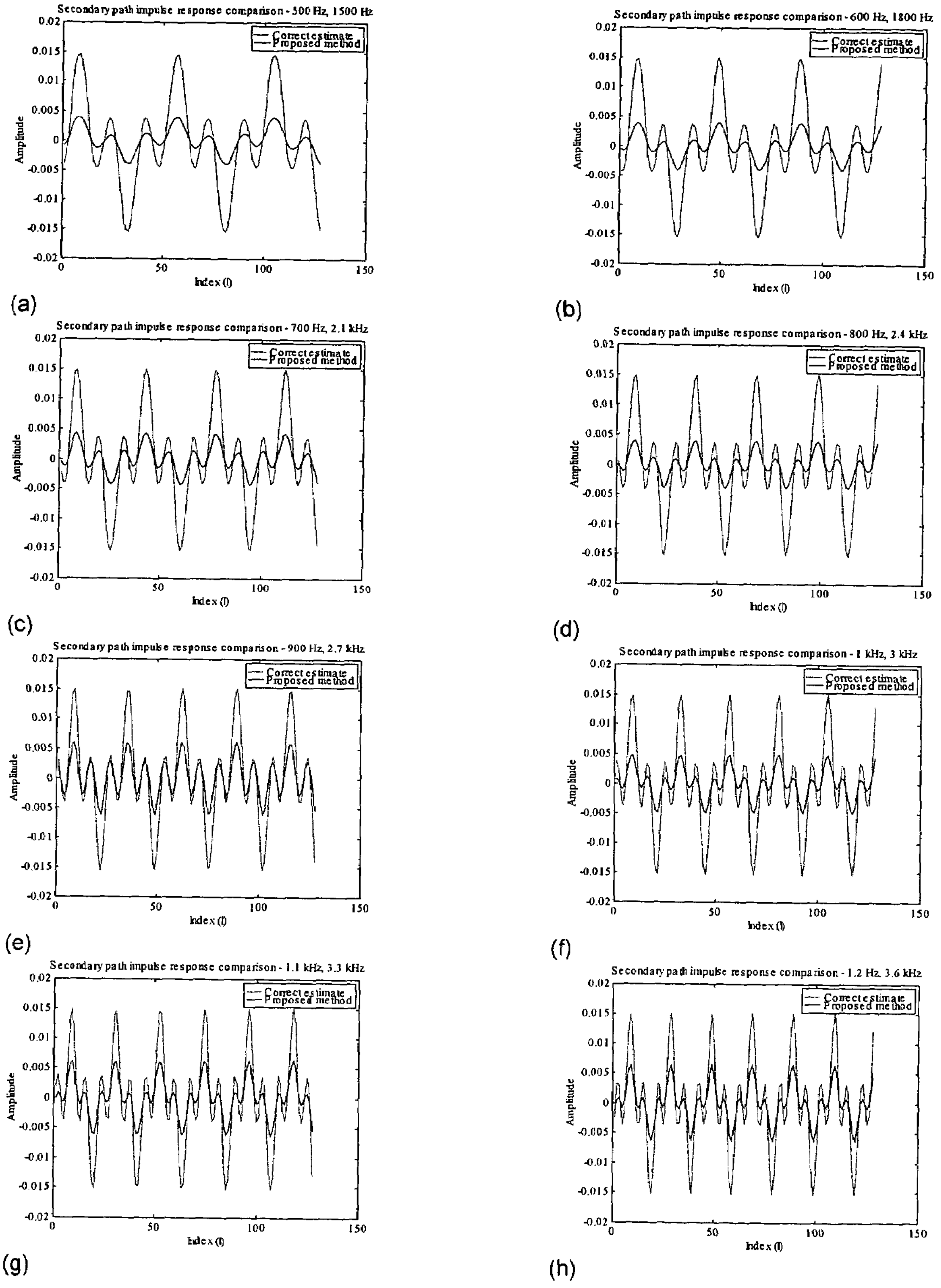
FIG. 25 is a secondary path impulse response estimate comparison for shifting frequencies during the operation of a system of the present invention.

The performance of this algorithm for this test is shown in FIG. 24. FIG. 24 shows the magnitude of the larger of two sinusoids in error signal as active controller adapts to changes in frequency in a stationary secondary path environment. The magnitude of the larger amplitude sinusoid in the error signal is given at each iteration where the magnitude is in volts. Next, FIG. 25, reveals the secondary path impulse response for each frequency shift as determined by the present method during system operation. FIG. 25 shows a secondary path impulse response estimate comparison for shifting frequencies during system operation. These are compared to the correct estimates. Again, the phases of the impulse responses correspond exactly. The amplitudes of the present method's impulse responses are consistently lower than the respective amplitudes of the correct estimates. And, as before, the filtered-X algorithm never went unstable as the frequencies shifted. This is, again, attributable to the accuracy of the secondary path estimates.

Figure 26:
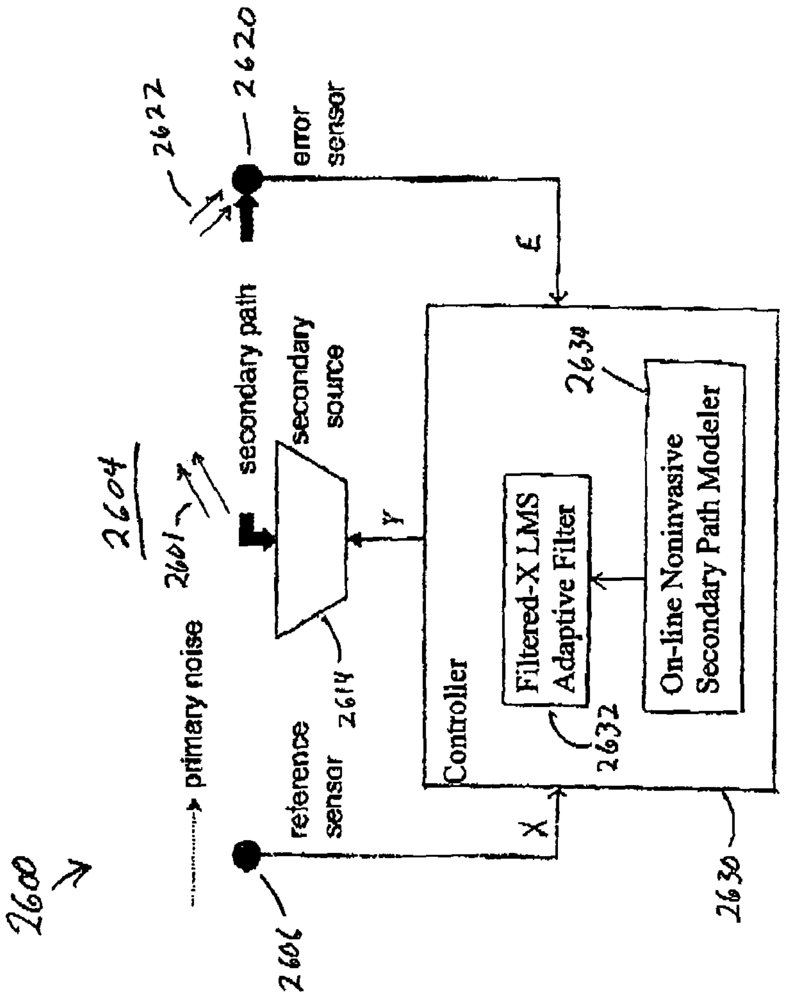
FIG. 26 is a system diagram of the active noise and vibration control system of the present invention.

Referring to FIG. 26, an active noise and vibration control system 2600 of the present invention generates an antinoise signal 2601 to attenuate a narrowband noise signal 2602 propagating through a medium 2604. Active noise and vibration control system 2600 performs on-line noninvasive secondary path modeling. Active noise and vibration control system 2600 comprises a reference sensor 2606, a secondary source 2614, an error sensor 2620 and a controller 2630. Reference sensor 2606 operates to receive a reference signal related to a primary noise 2610 and to generate a primary signal X in response. Secondary source 2614 operates to generate antinoise signal 2601 corresponding to a secondary signal Y that attenuates primary noise 2610. Error sensor 2620 is operable to receive a residual signal 2622 that is the superposition of the primary noise 2610 and secondary noise 2601 at the location of error sensor 2620, and to generate an error signal E in response thereto.

Controller 2630 operates to receive primary signal X and error signal E and to generate secondary signal Y while performing on-line noninvasive secondary path modeling. Controller 2630 comprises a filtered-XLMS adaptive filter 2632 and an on-line noninvasive secondary path modeler 2634. On-line noninvasive modeler 2634 is operable to receive primary signal X, secondary signal Y, and error signal E for the purpose of calculating the secondary path model that provides estimates of filter parameters to filtered-XLMS adaptive filter 2632 for making changes to filter coefficients thereof.

Although the invention has been shown and described in the manner set forth herein, those skilled in the art will recognize that the various features of this invention, as described herein, can be used in various combinations and with other elements without departing from the spirit and scope of the invention.

What is claimed is:

1. An active noise and vibration control system for generating an antinoise signal to attenuate a narrowband noise signal propagating through a medium, said active noise and vibration control system performing on-line noninvasive secondary path modeling, said system, comprising:

a reference sensor operable to receive a reference signal related to a primary noise and to generate a primary signal in response;

a secondary source operable to generate an antinoise corresponding to a secondary signal that attenuates the primary noise;

an error sensor operable to receive a residual signal that is a superposition of said primary noise and a secondary noise at the location of said error sensor, and to generate an error signal in response thereto; and a controller operable to receive said primary signal and said error signal and to generate said secondary signal while performing on-line noninvasive secondary path modeling, said controller comprising an on-line noninvasive secondary path modeler operable to receive said primary signal, said secondary signal, and said error signal for the purpose of calculating a secondary path model, wherein said online noninvasive secondary path modeler captures first and second data sets comprising said reference signal, said error signal and said generated secondary signal, to calculate a transfer function of a secondary path, and to alter an output of said secondary source by adjusting output filter coefficients of a control filter in amplitude, in phase, or in both amplitude and phase between acquisition of said first and second data sets, thereby imposing linear independence on said first and second data sets, wherein said secondary path modeler uses said control filter and said first and second data sets to calculate said secondary path model algebraically in a system of first and second equations-two unknowns, P(k) and S(k), as follows:

$$X_A(k)P(k)+Y_A(k)S(k)=E_A(k),$$

$$X_B(k)P(k)+Y_B(k)S(k)=E_B(k),$$

where $\{X_A(k),Y_A(k),E_A(k)\}$ corresponds to said first data set and $\{X_B(k),Y_B(k),E_B(k)\}$ corresponds to said second data set, $Y_A(k)$ and $Y_B(k)$ represent outputs of said control filter according to the equations:

$$Y_A(k)=W_A(k)X_A(k),$$

$$Y_B(k)=W_B(k)X_B(k),$$

where W(k) is the FFT of said control filter's impulse response, wherein said linear independence of said first and second equations is achieved by ensuring the inequality of $W_A(k)\neq W_B(k)$, wherein a solution of said first and second equations is given by:

$$\hat{P}(k) = \frac{E_A(k)Y_B(k) - Y_A(k)E_B(k)}{X_A(k)Y_B(k) - Y_A(k)X_B(k)},$$

$$\hat{S}(k) = \frac{X_A(k)E_B(k) - E_A(k)X_B(k)}{X_A(k)Y_B(k) - Y_A(k)X_B(k)},$$

and wherein an equation derived from said algebraic calculation is modified to account for spectral leakage and narrowband effects.

2. The system according to claim 1, wherein said derived equation is modified to account for multiple frequency signals, and frequency spectrum is divided into subbands to scale each frequency component separately.

3. A feedforward active noise and vibration control system, comprising:

a controller for receiving a primary signal and an error signal and generating a secondary signal in response thereto, said controller comprising: an adaptive filter utilizing block time-domain or equivalent frequency-domain processing, an on-line noninvasive secondary path modeler that captures first and second data sets comprising a reference signal, an error signal and generates said secondary signal, to calculate a transfer function of a secondary path, and to alter an output of a secondary source by adjusting output filter coefficients of said adaptive filter in amplitude, in phase, or in both amplitude and phase between acquisition of said first and second data sets, thereby imposing linear independence on said first and second data sets; wherein said secondary path modeler uses first and second data sets to calculate a secondary path model algebraically in a system of first and second equations-two unknowns, P(k) and S(k), as follows:

$$X_A(k)P(k)+Y_A(k)S(k)=E_A(k),$$

$$X_B(k)P(k)+Y_B(k)S(k)=E_B(k),$$

where $\{X_A(k),Y_A(k),E_A(k)\}$ corresponds to said first data set and $\{X_B(k),Y_B(k),E_B(k)\}$ corresponds to said second data set, $Y_A(k)$ and $Y_B(k)$ represent outputs of said control filter according to the equations:

$$Y_A(k)=W_A(k)X_A(k),$$

$$Y_B(k)=W_B(k)X_B(k),$$

where W(k) is the FFT of said control filter's impulse response, wherein said linear independence of said first and second equations is achieved by ensuring the inequality of $W_A(k)\neq W_B(k)$, wherein a solution of said first and second equations is given by:

$$\hat{P}(k) = \frac{E_A(k)Y_B(k) - Y_A(k)E_B(k)}{X_A(k)Y_B(k) - Y_A(k)X_B(k)},$$

$$\hat{S}(k) = \frac{X_A(k)E_B(k) - E_A(k)X_B(k)}{X_A(k)Y_B(k) - Y_A(k)X_B(k)},$$

and wherein an equation derived from said algebraic calculation is modified to account for spectral leakage and narrowband effects.

4. The system according to claim 3, further comprising:

an online noninvasive secondary path modeler to capture two data sets comprising a reference signal, an error signal and generated secondary signal, to calculate a transfer function of said secondary path, and to alter an output of a secondary source by adjusting output filter coefficients in amplitude, in phase, or in both amplitude and phase between acquisition of said data sets, thereby imposing linear independence on said data sets.

5. A method for calculating an accurate secondary path model, comprising:

employing an on-line noninvasive secondary path modeler to capture first and second data sets comprising a reference signal, an error signal and a generated secondary signal;

using said on-line noninvasive secondary path modeler to calculate the transfer function of a secondary path; and using said on-line noninvasive secondary path modeler to alter an output of a secondary source by adjusting output filter coefficients of a control filter in amplitude, in phase, or in both amplitude and phase between acquisition of said first and second data sets, thereby imposing linear independence on said first and second data sets, wherein said secondary path modeler uses said control filter and said first and second data sets to calculate said secondary path model algebraically in a system of first and second equations-two unknowns, P(k) and S(k), as follows:

$$X_A(k)P(k)+Y_A(k)S(k)=E_A(k),$$

$$X_B(k)P(k)+Y_B(k)S(k)=E_B(k),$$

where $\{X_A(k),Y_A(k),E_A(k)\}$ corresponds to said first data set and $\{X_B(k),Y_B(k),E_B(k)\}$ corresponds to said second data set, $Y_A(k)$ and $Y_B(k)$ represent outputs of said control filter according to the equations:

$$Y_A(k)=W_A(k)X_A(k),$$

$$Y_B(k)=W_B(k)X_B(k),$$

where W(k) is the FFT of said control filter's impulse response, wherein said linear independence of said first and second equations is achieved by ensuring the inequality of $W_A(k)\neq W_B(k)$, wherein a solution of said first and second equations is given by:

$$\hat{P}(k) = \frac{E_A(k)Y_B(k) - Y_A(k)E_B(k)}{X_A(k)Y_B(k) - Y_A(k)X_B(k)},$$

$$\hat{S}(k) = \frac{X_A(k)E_B(k) - E_A(k)X_B(k)}{X_A(k)Y_B(k) - Y_A(k)X_B(k)},$$

and wherein an equation derived from said algebraic calculation is modified to account for spectral leakage and narrowband effects.

6. The method according to claim 5, wherein said secondary path modeler is noninvasive.

7. The method according to claim 5, wherein said derived equation is modified to account for multiple frequency signals, and frequency spectrum is divided into subbands to scale each frequency component separately.

8. A method for on-line noninvasive secondary path modeling, comprising:

receiving, by a reference sensor, a reference signal related to a primary noise;

generating, by said reference sensor, a primary signal in response to said reference signal;

generating, by a secondary source, an antinoise corresponding to a secondary signal that attenuates the primary noise;

receiving, by an error sensor, a residual signal that is the superposition of said primary noise and a secondary noise at the location of said error sensor, and to generate an error signal in response thereto; and receiving, by a controller, said primary signal and said error signal;

generating, by said controller, said secondary signal while performing on-line noninvasive secondary path modeling, said controller comprising an on-line noninvasive secondary path modeler operable to receive said primary signal, said secondary signal, and said error signal for the purpose of calculating a secondary path model, wherein said online noninvasive secondary path modeler captures first and second data sets comprising said reference signal, said error signal and said generated secondary signal, to calculate a transfer function of a secondary path, and to alter an output of said secondary source by adjusting output filter coefficients of a control filter in amplitude, in phase, or in both amplitude and phase between acquisition of said first and second data sets, thereby imposing linear independence on said first and second data sets, wherein said secondary path modeler uses said control filter and said first and second data sets to calculate said secondary path model algebraically in a system of first and second equations-two unknowns, P(k) and S(k), as follows:

$$X_A(k)P(k)+Y_A(k)S(k)=E_A(k),$$

$$X_B(k)P(k)+Y_B(k)S(k)=E_B(k),$$

where $\{X_A(k),Y_A(k),E_A(k)\}$ corresponds to said first data set and $\{X_B(k),Y_B(k),E_B(k)\}$ corresponds to said second data set, $Y_A(k)$ and $Y_B(k)$ represent outputs of said control filter according to the equations:

$$Y_A(k)=W_A(k)X_A(k),$$

$$Y_B(k)=W_B(k)X_B(k),$$

where W(k) is the FFT of said control filter's impulse response, wherein said linear independence of said first and second equations is achieved by ensuring the inequality of $W_A(k)\neq W_B(k)$, wherein a solution of said first and second equations is given by:

$$\hat{P}(k)=\frac{E_A(k)Y_B(k)-Y_A(k)E_B(k)}{X_A(k)Y_B(k)-Y_A(k)X_B(k)},$$

$$\hat{S}(k)=\frac{X_A(k)E_B(k)-E_A(k)X_B(k)}{X_A(k)Y_B(k)-Y_A(k)X_B(k)},$$

and wherein an equation derived from said algebraic calculation is modified to account for spectral leakage and narrowband effects.

9. A method for feedforward active noise and vibration control, comprising:

receiving, by a controller, a primary signal and an error signal and generating a secondary signal in response thereto, said controller comprising: an adaptive filter utilizing block time-domain or equivalent frequency-domain processing, an on-line noninvasive secondary path modeler that captures first and second data sets comprising a reference signal, an error signal and generates said secondary signal, to calculate a transfer function of a secondary path, and to alter an output of a secondary source by adjusting output filter coefficients of said adaptive filter in amplitude, in phase, or in both amplitude and phase between acquisition of said first and second data sets, thereby imposing linear independence on said first and second data sets; wherein said secondary path modeler uses said adaptive filter and said first and second data sets to calculate a secondary path model algebraically in a system of first and second equations-two unknowns, P(k) and S(k), as follows:

$$X_A(k)P(k)+Y_A(k)S(k)=E_A(k),$$

$$X_B(k)P(k)+Y_B(k)S(k)=E_B(k),$$

where $\{X_A(k),Y_A(k),E_A(k)\}$ corresponds to said first data set and $\{X_B(k),Y_B(k),E_B(k)\}$ corresponds to said second data set, $Y_A(k)$ and $Y_B(k)$ represent outputs of said control filter according to the equations:

$$Y_A(k)=W_A(k)X_A(k),$$

$$Y_B(k)=W_B(k)X_B(k),$$

where W(k) is the FFT of said control filter's impulse response, wherein said linear independence of said first and second equations is achieved by ensuring the inequality of $W_A(k)\neq W_B(k)$, wherein a solution of said first and second equations is given by:

$$\hat{P}(k)=\frac{E_A(k)Y_B(k)-Y_A(k)E_B(k)}{X_A(k)Y_B(k)-Y_A(k)X_B(k)},$$

$$\hat{S}(k)=\frac{X_A(k)E_B(k)-E_A(k)X_B(k)}{X_A(k)Y_B(k)-Y_A(k)X_B(k)},$$

and wherein an equation derived from said algebraic calculation is modified to account for spectral leakage and narrowband effects.

* * * * *

UNITED STATES PATENT AND TRADEMARK OFFICE

CERTIFICATE OF CORRECTION

PATENT NO. : 7,343,016 B2
APPLICATION NO. : 10/619801
DATED : March 11, 2008
INVENTOR(S) : Benjamin Jung Kim It is certified that error appears in the above-identified patent and that said Letters Patent is hereby corrected as shown below:

ON THE TITLE PAGE ITEM

(75) Please correct residence of Inventor Benjamin Jung Kim to read "State College, PA (US)"

IN THE DESCRIPTION

Column 1,
Line 14, after "...periodic noise." please add the following heading and paragraph from Line 15 and following:

--FEDERALLY SPONSORED RESEARCH AND DEVELOPMENT

This invention was made with government support under Contract No. N00039-97-D-0042, Delivery Order No. 227, awarded by the Naval Sea Systems Command. The Government has certain rights in the invention.--

Signed and Sealed this

Seventeenth Day of June, 2008

Jon W. Dudas

JON W. DUDAS
*Director of the United States Patent and Trademark Office*

UNITED STATES PATENT AND TRADEMARK OFFICE

CERTIFICATE OF CORRECTION

PATENT NO. : 7,343,016 B2
APPLICATION NO. : 10/619801
DATED : March 11, 2008
INVENTOR(S) : Benjamin Jung Kim It is certified that error appears in the above-identified patent and that said Letters Patent is hereby corrected as shown below:

On the title page item (73) Please correct residence of Assignee The Penn State Research Foundation to read --University Park, PA (US)--

Signed and Sealed this

Eighth Day of July, 2008

JON W. DUDAS
*Director of the United States Patent and Trademark Office*

UNITED STATES PATENT AND TRADEMARK OFFICE

CERTIFICATE OF CORRECTION

PATENT NO. : 7,343,016 B2
APPLICATION NO. : 10/619801
DATED : March 11, 2008
INVENTOR(S) : Benjamin Jung Kim It is certified that error appears in the above-identified patent and that said Letters Patent is hereby corrected as shown below:

ON THE TITLE PAGE

ITEM (73) Residence of Assignee The Penn State Research Foundation should read --University Park, PA (US)--

Signed and Sealed this

Twenty-second Day of July, 2008

JON W. DUDAS
*Director of the United States Patent and Trademark Office*